United States Patent
Troncelliti et al.

(10) Patent No.: US 11,872,033 B2
(45) Date of Patent: Jan. 16, 2024

(54) METHODS AND DEVICES FOR VISUALIZING ANALYTE MEASUREMENTS

(71) Applicant: Lifescan IP Holdings, LLC, Malvern, PA (US)

(72) Inventors: Lisa Troncelliti, Malvern, PA (US); Mark Hofmeister, Malvern, PA (US); Allison Gonzales, San Jose, CA (US); David Shearer, Malvern, PA (US); Brian Levy, New York, NY (US); Bovornrat K. Cochard, Oakland, CA (US)

(73) Assignee: Lifescan iP Holdings, LLC, Malvern, PA (US)

( * ) Notice: Subject to any disclaimer, the term of this patent is extended or adjusted under 35 U.S.C. 154(b) by 156 days.

(21) Appl. No.: 17/096,173

(22) Filed: Nov. 12, 2020

(65) Prior Publication Data
US 2021/0161436 A1  Jun. 3, 2021

Related U.S. Application Data

(60) Provisional application No. 62/935,888, filed on Nov. 15, 2019.

(51) Int. Cl.
*A61B 5/145* (2006.01)
*A61B 5/00* (2006.01)

(52) U.S. Cl.
CPC ........ *A61B 5/14532* (2013.01); *A61B 5/7275* (2013.01); *A61B 5/742* (2013.01); *A61B 5/7435* (2013.01)

(58) Field of Classification Search
CPC . A61B 5/14532; A61B 5/7435; A61B 5/7275; A61B 5/742
See application file for complete search history.

(56) References Cited

U.S. PATENT DOCUMENTS 10,188,796 B2    1/2019  Chovanda et al.
2014/0244292 A1*  8/2014  Rosenberg ............. G16H 70/00
                                                   705/2

(Continued)

FOREIGN PATENT DOCUMENTS

WO    WO 2010/111660 A1    9/2010

OTHER PUBLICATIONS

International Search Report and Written Opinion for PCT/US2020/060365; dated Feb. 18, 2021; 9 pages.

(Continued)

*Primary Examiner* — David J. McCrosky
*Assistant Examiner* — Clarissa Cuevas
(74) *Attorney, Agent, or Firm* — Barclay Damon LLP

(57) ABSTRACT

Systems, methods and graphical user interfaces for visualizing analyte measurements using animation are presented. For instance, a system for continuously monitoring analyte concentration in a physiological fluid includes a sensor, a transmitter, at least one processor and a display. The display is for outputting a graphical user interface. The display is controlled by the at least one processor to display, using the graphical user interface, historical analyte concentration levels and a trend indication animation. The trend indication animation comprises at least one visual element configured by the at least one processor to have a periodic motion between a first position and a second position on the display in one of a plurality of trend directions. The trend direction of the periodic motion between the first and second positions indicates whether the analyte concentration is increasing or decreasing and the rate of change of the analyte concentration level. The at least one visual element is further configured with a period of the periodic motion between the first and second positions in order to indicate a severity of an excursion of the analyte concentration.

18 Claims, 21 Drawing Sheets

(56) References Cited

U.S. PATENT DOCUMENTS

2016/0183795 A1* 6/2016 Cowley ................. A61B 5/746
                                                    340/870.02
2017/0046052 A1* 2/2017 Lee ...................... G06F 3/0488
2018/0042558 A1   2/2018 Cabrera, Jr. et al.
2018/0296757 A1  10/2018 Finan et al.

OTHER PUBLICATIONS

Canadian Intellectual Property Office; Canadian Application No. 3,161,715; dated Aug. 16, 2023; 4 pages.

* cited by examiner

X=High Limit of the user's target glucose range
Y=Low Limit of the user's target glucose range
* This condition overrides others

| | 501+ Extreme High | 500-300 Very High | 299-X High | User's target glucose range In Range | Y-56 Low | 55-40 Very Low | 39-0 Extreme Low | Urgent Low Soon * |
|---|---|---|---|---|---|---|---|---|
| ↓ Rapidly Falling | — | L1 | L0 | L1 | L3 | L3 | — | L3 |
| ↓ Falling | — | L1 | L0 | L1 | L3 | L3 | — | L3 |
| ↘ Slowly Falling | — | L1 | L0 | L1 | L3 | L3 | — | L3 |
| → Steady | — | L2 | L1 | L0 | L1 | L3 | — | |
| ↗ Slowly Rising | — | L3 | L2 | L1 | L0 | L2 | — | |
| ↑ Rising | — | L3 | L2 | L1 | L0 | L2 | — | |
| ↑ Rapidly Rising | — | L3 | L2 | L1 | L0 | L2 | — | |
| No Arrow One bubble pulsing | L2 | L2 | L1 | L1 | L2 | L2 | L2 | L2 |

| Level | L0 | L1 | L2 | L3 |
|---|---|---|---|---|
| Animation | Slow | Fast | Super Fast | Super Fast + Blinking |
| Duration | 2 sec. | 1 sec. | 0.4 sec. | 0.4 sec. |

*FIG. 24*

METHODS AND DEVICES FOR VISUALIZING ANALYTE MEASUREMENTS

CROSS-REFERENCE TO RELATED APPLICATION(S)

This application claims priority to U.S. Provisional Patent Application Ser. No. 62/935,888, filed Nov. 15, 2019, which is incorporated herein by reference in its entirety.

TECHNICAL FIELD

This application is directed to the field of analyte measurement and more specifically to systems, methods and devices for visualizing analyte measurements, including alerting users of events.

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e., the presence of an excessive amount of glucose in the blood plasma. Persistent hyperglycemia and/or hypoinsulinemia has been associated with a variety of serious symptoms and life threatening long term complications such as dehydration, ketoacidosis, diabetic coma, cardiovascular diseases, chronic renal failure, retinal damage and nerve damages with the risk of amputation of extremities.

Blood or interstitial glucose monitoring is required to achieve acceptable glycemic control. Continuous glucose monitoring (CGM) has been utilized over the last twenty years for such glucose monitoring. CGM creates data that is much more abundant and complex than that of traditional, episodic glucose monitoring. This added complexity may overwhelm users of the devices, as well as caregivers and health care practitioners ("HCPs"), especially in the absence of a suitable tool to assist in the interpretation of such data.

BRIEF DESCRIPTION

Therefore, in one embodiment, a device for continuously monitoring analyte concentration in a physiological fluid is presented. The device comprises a sensor, a transmitter, at least one processor and a display. The display is configured for outputting a graphical user interface. The display is controlled by the at least one processor to display, using the graphical user interface, historical analyte concentration levels and a trend indication animation. The trend indication animation comprises a visual element configured by the at least one processor to have a periodic motion between a first position and at least a second position on the display in one of a plurality of trend directions. The trend direction of the periodic motion between the first and second positions indicates whether the analyte concentration is increasing or decreasing and the rate of change of the analyte concentration level. The visual element is further configured with a period of the periodic motion between the first and second positions in order to indicate a severity of an excursion of the analyte concentration, as compared with the target analyte concentration level.

In another embodiment, a method for alerting a user of an event related to an analyte concentration in a physiological fluid is presented. The method includes the acts of continuously monitoring an analyte concentration of the physiological fluid and displays, using a graphical user interface, historical analyte concentration levels and a trend indication animation. The trend indication animation comprises a visual element configured by the at least one processor to have a periodic motion between a first position and a second position on the display in one of a plurality of trend directions. The trend direction of the periodic motion between the first and second positions indicates whether the analyte concentration is increasing or decreasing. The visual element is further configured with a period of the periodic motion between the first and second positions in order to indicate a severity of an excursion or predicted excursion of the analyte concentration, as compared with the target analyte concentration level.

In a further embodiment, presented herein is a graphical user interface for alerting a user of events based on continuous monitoring of an analyte concentration in a physiological fluid. The graphical user interface displays historical analyte concentration levels and a trend indication animation. The trend indication animation comprises a visual element configured by the at least one processor to have a periodic motion between a first position and a second position on the display in one of a plurality of trend directions. The trend direction of the periodic motion between the first and second positions indicates whether the analyte concentration is increasing or decreasing. The visual element is further configured with a period of the periodic motion between the first and second positions in order to indicate a severity of an excursion of the analyte concentration, as compared with the target analyte concentration level.

Advantages realized in one or more embodiments of the present disclosure include providing users with real-time feedback that alerts users to potentially dangerous excursions and allows corrective action to be taken. Additional advantages include synthesizing large amounts of data into easy to understand, actionable information.

The above embodiments are exemplary only. Other features and advantages will be evident from the following Detailed Description as well as the accompanying drawings.

BRIEF DESCRIPTION OF THE DRAWINGS

So that the manner in which the features of the disclosure can be understood, a detailed description may be had by reference to certain embodiments, some of which are illustrated in the accompanying drawings. It is to be noted, however, that the drawings illustrate only certain embodiments and are therefore not to be considered limiting of its scope, for the scope of the disclosed subject matter encompasses other embodiments as well. The drawings are not necessarily to scale, emphasis generally being placed upon illustrating the features of certain embodiments. In the drawings, like numerals are used to indicate like parts throughout the various views.

FIG. 24 depicts an embodiment of an animation decision matrix for determining which animated graphical user interface to present on the display unit of FIG. 1, and in accordance with one or more aspects set forth herein;

Corresponding reference characters may indicate corresponding parts throughout several views as presented herein. In addition, the various examples set out herein illustrate several embodiments, but should not be construed as limiting in scope in any manner.

DETAILED DESCRIPTION

Figure 1:
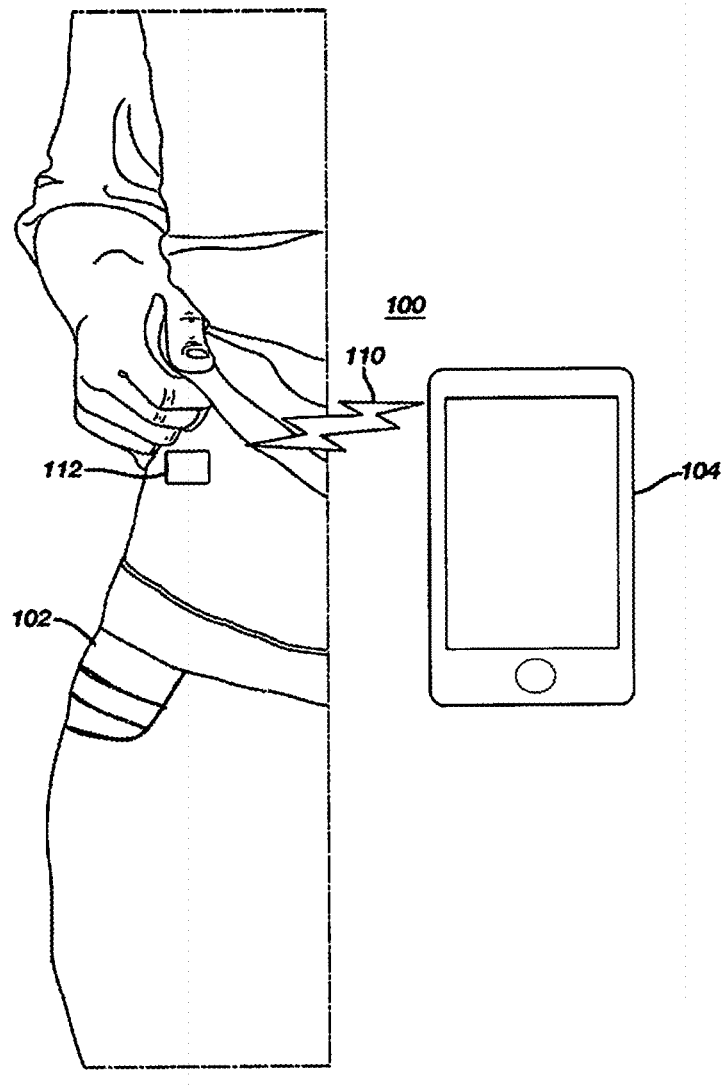
FIG. 1 depicts an example of a continuous glucose monitoring sensor in communication via a transmitter with a display unit.

The present disclosure relates to a continuous glucose monitoring system (a "CGM" system) in which an enhanced graphical user interface is provided. Unlike conventional, static user interfaces, the present invention provides animations that better convey and indicate trends in the analyte concentration levels of a user at a minimum. Advantageously, enhanced visualizations, such as animated graphical user interfaces, are a practical enhancement in the field of glucometry that can simplify the communication of information to the user to better facilitate prompt response to events involving an individual.

Conventional systems that provide static reports or centralized reports are not able to meet the real-time needs of a user who is engaged in a treatment plan, e.g., for diabetes mellitus. Advantageously, the present disclosure improves patient outcomes, reduces patient anxiety, and better allows the CGM equipment to perform in a manner that meets the patient's treatment plan. In addition, the present disclosure offers the ability to respond in real-time to potentially dangerous or life-threatening excursions.

Conventional analyte monitoring systems are limited in the ways in which they can display information. Such systems are also static in nature. A large amount of information is available to the system, and simply displaying all the data without synthesis makes it difficult for the user to find useful information. For example, conventional techniques of organizing analyte monitoring data include creating a series of menus that a user must navigate to find information, hampering the utility of such systems. Advantageously, in one aspect, the present disclosure provides a technique for synthesizing large amounts of complex data into actionable, easy to use information, that is delivered at the point of impact to the user. Specifically, by tying together trend data and analyte value data into animations, the present disclosure allows data that was conventionally displayed separately to be unified into a single display to the user, solving the problems identified in conventional systems.

In a CGM system, glucose levels or concentrations can be determined by the use of a continuous glucose monitoring (CGM) sensor. The CGM sensor utilizes, for example, amperometric electrochemical sensor technology to measure glucose with electrodes such as a working electrode and a counter electrode, operably connected to the sensor electronics that are covered by a sensing membrane and a biointerface membrane, which are attached by a clip. Examples of such systems are found, for example, in U.S. Pat. No. 10,188,796 B2 and U.S. Patent Application Publication No. 2018/0296757 A1, each of which are herein incorporated by reference in their entirety.

The top ends of the electrodes are in contact with an electrolyte phase (not shown), which is a free-flowing fluid phase disposed between the sensing membrane and the electrodes. The sensing membrane may include an enzyme, e.g., glucose oxidase, which covers the electrolyte phase. In this exemplary sensor, the counter electrode is provided to balance the current generated by the analyte species being measured at the working electrode. For example, in the case of a glucose oxidase based glucose sensor, the species being measured at the working electrode is $H_2O_2$. The current that is produced at the working electrode (and flows through the circuitry to the counter electrode) is proportional to the diffusional flux of $H_2O_2$ generated by this electrochemical transformation of glucose into its enzymatic byproducts. Accordingly, a raw signal may be produced that is representative of the concentration of glucose in the user's body, and therefore may be utilized to estimate a meaningful glucose concentration value.

FIG. 1 depicts a system 100 for continuous glucose monitoring of a host 102. The system 100 includes an analyte (e.g., glucose) sensor 112, which transmits analyte concentration level values via wireless transmission 110 to a display unit 104. The display unit 104 could be a custom built unit, a smart phone, a tablet, or any other wirelessly enabled mobile or fixed device that includes a display and at least one processor for receiving and processing data from the analyte sensor 112. In one example, the display unit 104, including the at least one processor thereof, receives, stores, and analyzes data from the analyte sensor 112. For example, the device may be smart phone, e.g., an iPhone available from Apple Inc., of California, and include an ARM microprocessor. In such a case the smart phone may be running an application or app, which performs the functionality of the display unit 104 described herein.

The analyte sensor 112 may be coupled with an electronics module that includes a wireless transceiver for facilitating communication with the display unit 104. In another example, the sensor and transceiver may be part of a combined component. In one embodiment, the display unit 104 may include a touchscreen for input, and may run an operating system for hosting the graphical user interfaces described below. The analyte sensor 112 may be a continuous glucose monitoring sensor of any kind, such as those applied subcutaneously, transdermally, transcutaneously, including but not limited to implantable or other types. The continuous glucose monitoring sensor sends a data stream that includes the level of glucose concentration in the host 102. The display unit 104 is capable of receiving, storing, and processing this data stream. For instance, various algorithms known in the art may run on the at least one processor of the display unit 104 to process the data stream, etc.

It should be understood that the specific glucose analyte measurement examples set forth herein are meant to illustrate a specific implementation and not limit the disclosure in any way. The techniques described herein may be used to visualize continuous analyte measurements for other configurations than that depicted in FIG. 1, e.g., using other sensors for glucose or other analytes found in an interstitial fluid.

FIGS. 2A-23B depict various embodiments of animated graphical user interfaces presented on the display unit 104 of FIG. 1 for visualizing analyte measurements. By way of overview of FIGS. 2A-23B, each pair of figures, such as FIGS. 2A&2B, etc., represent a single exemplary user interface screen with animated visualizations depicted in two different states.

Figure 2A:
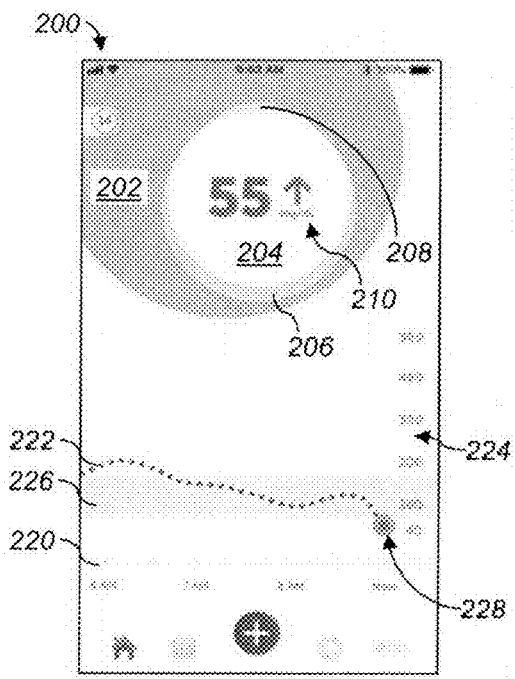
FIGS. 2A-23B depict embodiments of animated graphical user interfaces presented on the display unit of FIG. 1 for visualizing various analyte measurements as well as trended information, in accordance with one or more aspects set forth herein.
Figure 2B:
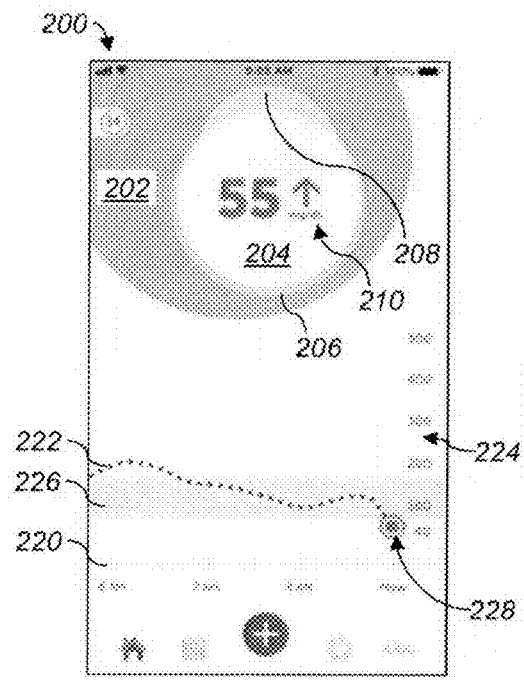

For example, FIGS. 2A & 2B depict a graphical user interface 200 as presented on the display unit. In an upper portion, the graphical user interface 200 includes a colored bubble 202, a white bubble 204, a first trend indicating bubble 206, a second trend indicating bubble 208, and a trend indicating arrow 210.

The color of the colored bubble 202 is configured to change in order to represent whether the current analyte concentration level is above, below, or at the target analyte concentration level as stored by the processor. In some embodiments, a determination that the level is at a target level or range would be based on the level being within a range of values. Levels below the target or target range, as here, are represented by a blue colored bubble, levels above the target analyte concentration level are represented by a red colored bubble, and levels at the target analyte concentration level are represented by a green colored bubble. The white bubble 204, as shown in the herein depicted embodiment, is static and includes near the center of the bubble 204, a current analyte concentration level numerical value. In other embodiments, the concentration level may be depicted using other visual cues, such as by a cluster of dots or objects, a bar of a bar chart embedded in the bubble, a number located in a different portion of the bubble, and the like.

Next and still referring to FIGS. 2A and 2B, the two trend indicating bubbles 206, 208, are disposed beneath the white bubble 204. As may be seen in FIG. 2A, the trend indicating bubble 206 emerges below the white bubble 204, and the second trend indicating bubble 208 emerges above the white bubble 204. As indicated in FIG. 2A, the first and second trend indicating bubbles 206, 208 move upward. In addition to the bubbles 202, 204, 206, 208, the graphical user interface 200 includes an arrow indicator 210, which may include a single arrow, double arrow, blinking arrow(s), and any other directional indicator. In some examples, the arrows may also move to indicate the direction of the trend. In other examples, if animation is turned off, one of the pair bubble images used to show the animation, i.e., FIGS. 2A, 3A, 4A, etc., may appear as static images, and will still serve as a directional indication to the user.

In the graphical user interface 200, trend indication animations are displayed to a user by the graphical user interface 200 periodically oscillating between the state of FIG. 2A and the state of FIG. 2B, with transitions between the states now described. A complete animation of graphical user interface 200 includes the first and second trend indicating bubbles 206 208 starting from the position shown in FIG. 2A, each bubble 206, 208 moving upward to the position of FIG. 2B, and then returning downward to the position of FIG. 2A. The upward direction of this movement indicates that the predicted trend of the analyte concentration level is rising. The direction of the arrow indicator 210 in combination with the displayed current analyte concentration level in the white bubble 204 indicates the severity of this rise. For example, an arrow indicator 210 in the upward direction combined with a displayed analyte concentration value of 300 mg/dL indicates a severe glycemic event, while an arrow indicator 210 in the downward direction along with a displayed analyte concentration value of 300 mg/dL indicates that the condition is not severe in that the analyte (glucose) concentration is trending back to the user's target range. Additionally, the speed at which the movement is taking place provides additional information about the severity of the glycemic event. For example, a faster rise is represented by a faster movement of the bubbles 206, 208. As programmed by the processor, this movement can be repeated at a periodic interval lasting anywhere from fractions of a second to several seconds in order to indicate the severity of the trend being displayed. For example, the faster the period, the more severely the analyte (glucose) concentration of the host is rising. In addition, more severe trends can be indicated in the graphical user interface by the use of a double arrow (or other) instead of the single arrow indicator 210.

In addition to the upper portion of FIG. 2A, the herein described graphical user interface 200 also includes a lower portion. The lower portion of the exemplary graphical user interface 200 includes a timeline 220, a historical graph 222, axis labels 224, a target analyte concentration band 226, and a current analyte reading animation 228. The current analyte reading animation 228, which may also be referred to as a "now dot" because it gives the current reading, is configured to oscillate between the depiction of FIG. 2A and FIG. 2B, e.g., along with the oscillation of the upper portion animation described above. In one or more embodiments, current analyte reading animation 228 (or "now dot") can disappear to indicate a lack of connectivity or can change colors, flash at different rates, etc., to where the colors are rates are indicative of conditions such as analyte concentration levels with respect to concentrations, etc. In addition, an icon can be further presented in the graphical user interface 200 to indicate the loss of connectivity. In other embodiments, a broken link icon may be displayed after some period of absent data, e.g., one minute. In such a case, the broken link icon may indicate loss of connection or indicate that the sensor is connected but is delivering unstable (e.g., invalid or nonactionable) readings.

In one embodiment, the animation described herein is implemented in such a way that the image depicted in FIG. 2A smoothly transitions to the image depicted in FIG. 2B, with the respective bubbles and other elements morphing their shapes from the condition depicted in FIG. 2A to the condition depicted in FIG. 2B, and then back again. A person of ordinary skill in the art can readily implement the specific animation that cycles between FIGS. 2A & 2B using any convenient programming tool available for implementing user interfaces or applications on either a standalone mobile device or a smart phone.

Having thus described the graphical user interface with respect to the examples of FIGS. 2A & 2B, further variations are now discussed with respect to FIGS. 3A-23B, with just the salient points highlighted.

Figure 3A:
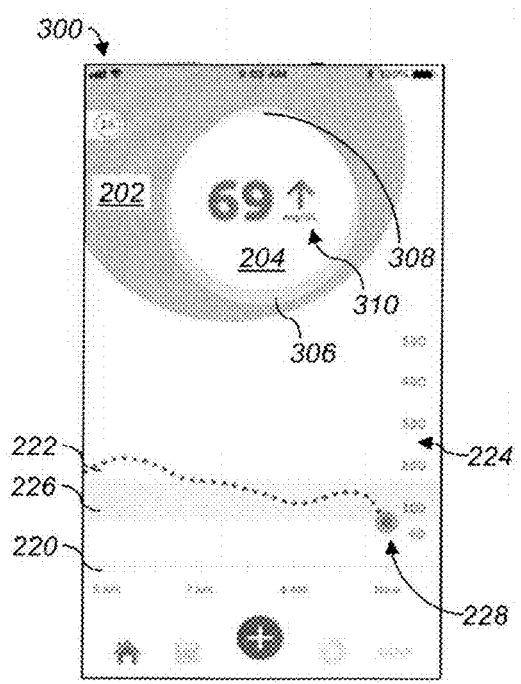
Figure 3B:
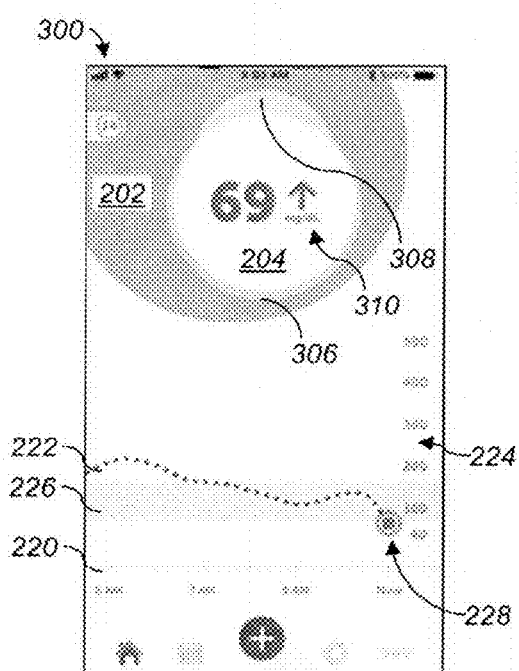

FIGS. 3A & 3B depict a graphical user interface 300. The animation includes periodically oscillating between the state of FIG. 3A and FIG. 3B. In this embodiment, first and second trend indicating bubbles 306, 308, are configured to move upward to indicate an upward trend in the analyte concentration level, and the period of the periodic movement may be different than that shown in FIGS. 2A & 2B.

Figure 4A:
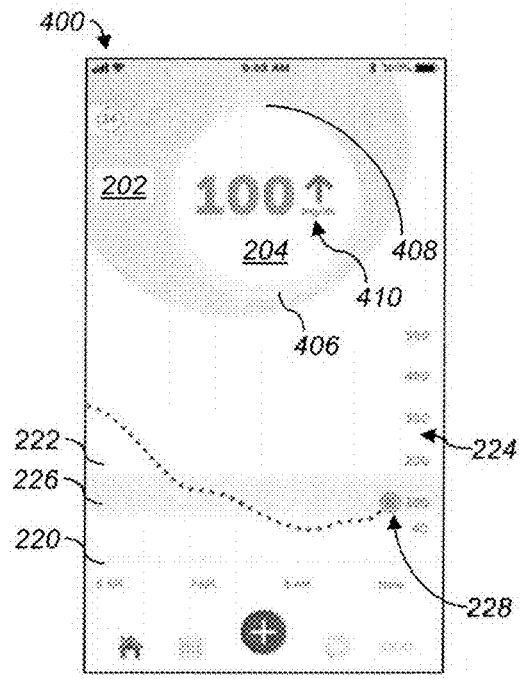
Figure 4B:
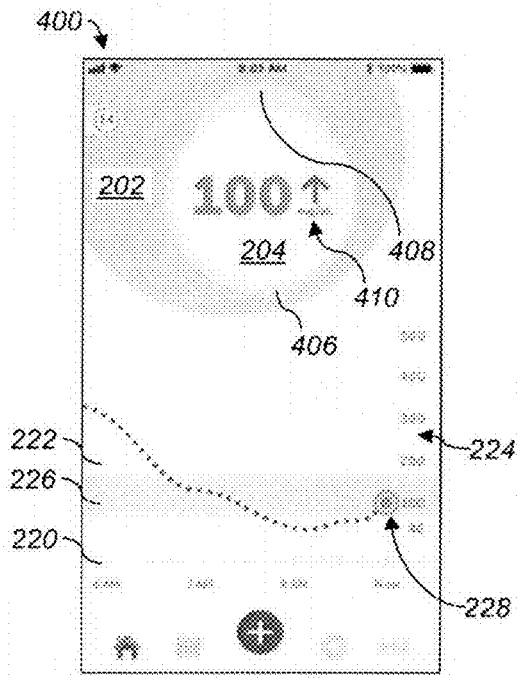

FIGS. 4A & 4B depict a graphical user interface 400. The animation includes periodically oscillating between the state of FIG. 4A and FIG. 4B. In this specific embodiment, the colored bubble 202 is green, indicating that the current analyte concentration level is at target. In addition, first and second trend indicating bubbles 406, 408, are configured to move upward to indicate an upward trend in the analyte (glucose) concentration level of the host, and an upward arrow indicator 410 is further provided, the latter being configured to indicate an upward trend in the analyte concentration level.

Figure 5A:
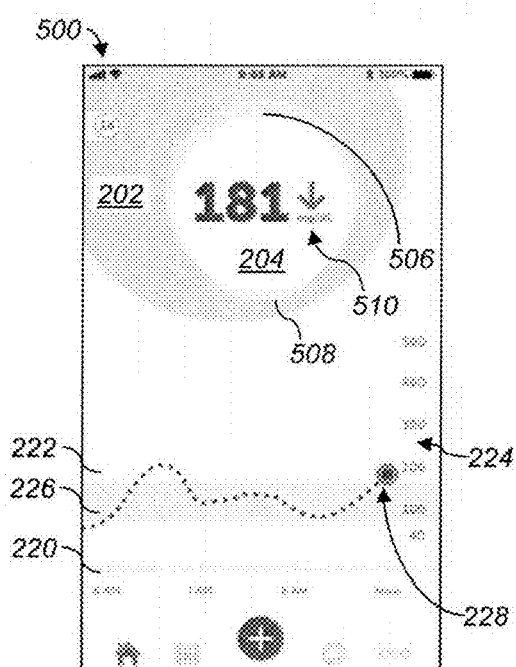
Figure 5B:
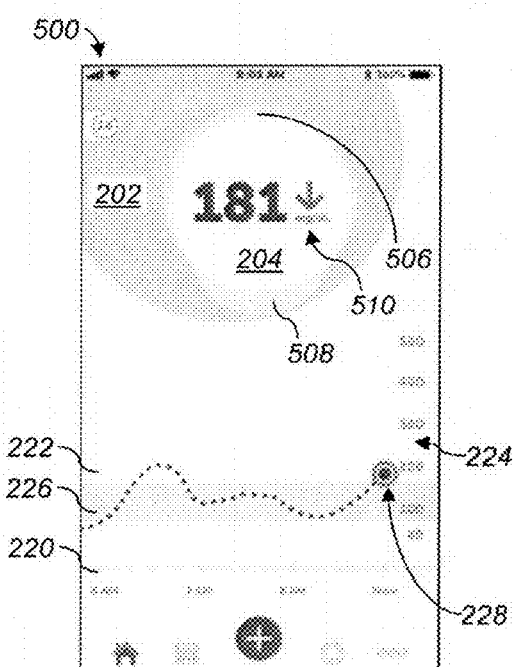

FIGS. 5A & 5B depict another version/embodiment of a graphical user interface 500 in accordance with the invention. The animation includes periodically oscillating between the state of FIG. 5A and FIG. 5B. In this embodiment, the colored bubble 202 is red, indicating that the current analyte concentration level is above target. In addition, first and second trend indicating bubbles 506, 508, are configured to move downward to indicate a downward trend in the analyte (glucose) concentration level of the host, and a downward arrow indicator 510 is further provided, the latter indicator 510 being configured to indicate a downward trend in the analyte concentration level.

Figure 6A:
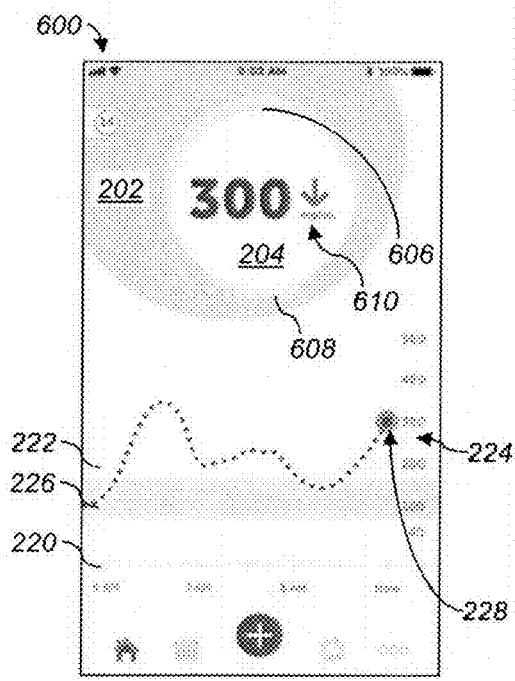
Figure 6B:
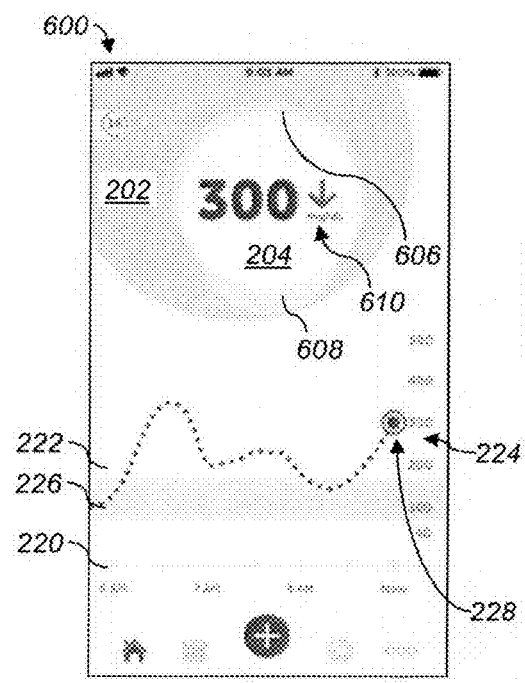

FIGS. 6A & 6B depict another version of a graphical user interface 600 in accordance with aspects of the invention. The animation includes periodically oscillating between the state of FIG. 6A and FIG. 6B. In this specific embodiment, the colored bubble 202 is red, indicating that the current analyte concentration level is above target. In addition, first and second trend indicating bubbles 606, 608, move downward to indicate a downward trend in the analyte concentration level, and a downward arrow indicator 610 is further provided, the latter indicator 610 being configured to indicate a downward trend in the analyte concentration level.

Figure 7A:
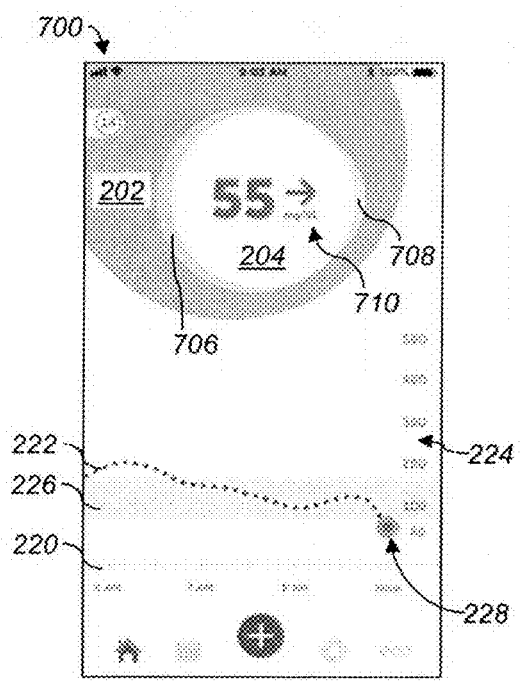
Figure 7B:
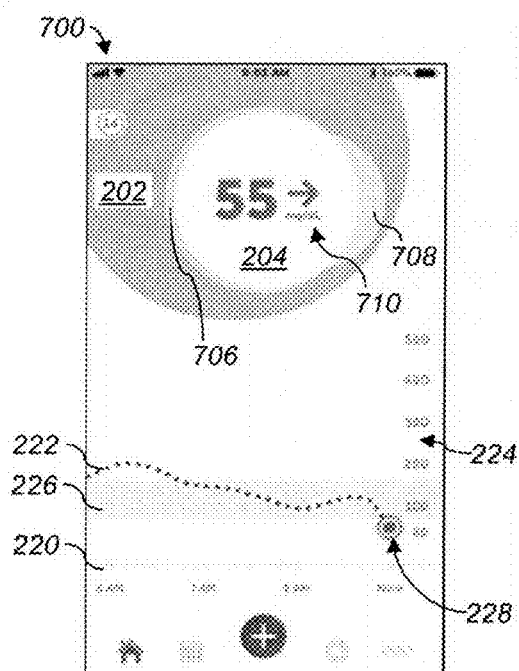

FIGS. 7A & 7B depict another graphical user interface 700 in accordance with aspect of the invention. The animation includes periodically oscillating between the state of FIG. 7A and FIG. 7B. In this embodiment, the colored bubble 202 is blue, indicating that the current analyte concentration level is below the target analyte (glucose) concentration level. In addition, first and second trend indicating bubbles 706, 708, are configured to move to the right, as shown, and a right arrow indicator 710 is provided, the latter indicators 706, 708, 710 being configured to indicate a stable trend in the analyte concentration level.

Figure 8A:
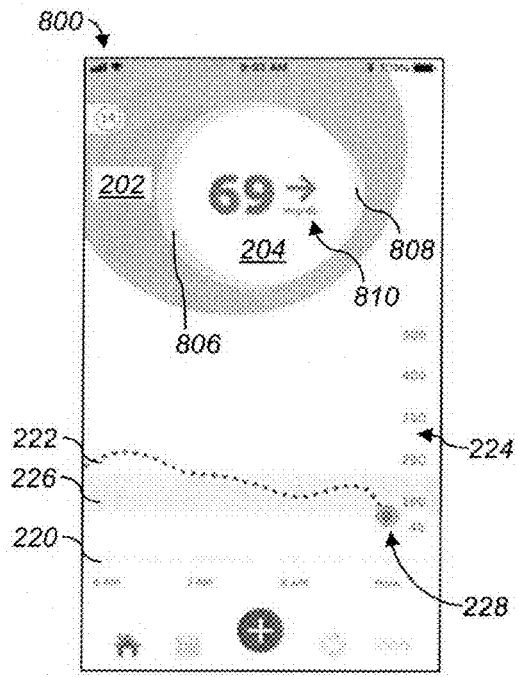
Figure 8B:
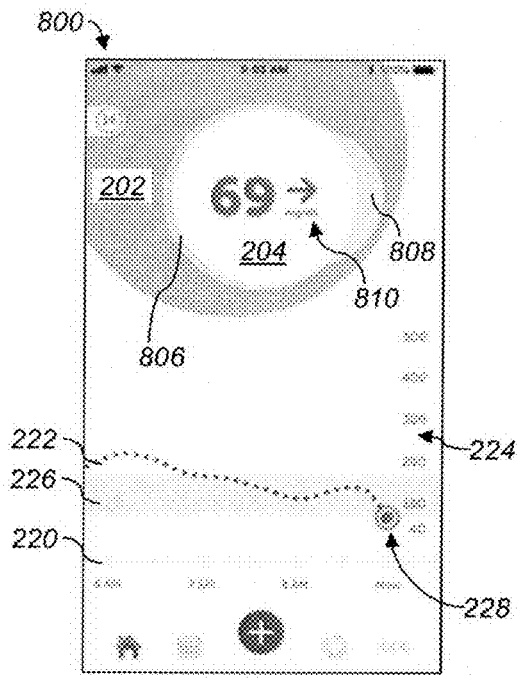

FIGS. 8A & 8B depict a graphical user interface 800 in accordance with other aspects of the invention. The animation includes periodically oscillating between the state of FIG. 8A and FIG. 8B. In this embodiment, the colored bubble 202 is blue, indicating that the current analyte concentration level is below the target analyte concentration level stored by the processor. In addition, first and second trend indicating bubbles 806, 808, are configured according to this example to move to the right, as shown, and a right arrow indicator 810 is provided, the latter bubbles and indicator 810 being configured to indicate or present to a user a stable trend in the analyte concentration level.

Figure 9A:
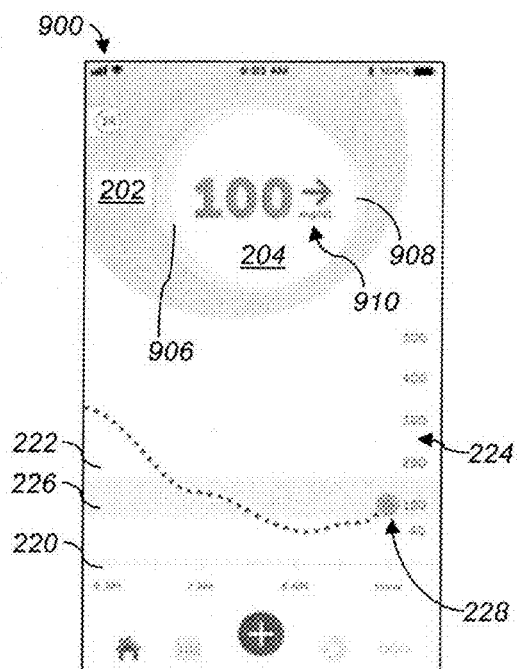
Figure 9B:
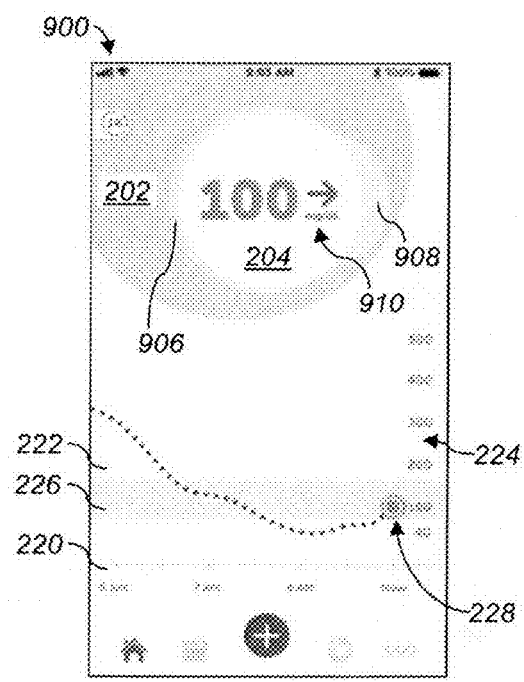

FIGS. 9A & 9B depict yet another graphical user interface 900 in accordance with aspects of the invention. The animation includes periodically oscillating between the state of FIG. 9A and FIG. 9B. In this specific embodiment, the colored bubble 202 is green, indicating that the current analyte concentration level is at the target analyte concentration level. In addition, first and second trend indicating bubbles 906, 908, are configured to move to the right in this animation, and a right arrow indicator 910 is provided, each of the bubbles 906, 908 and indicator 910 being configured in order to indicate a stable trend in the analyte concentration level to a user.

Figure 10A:
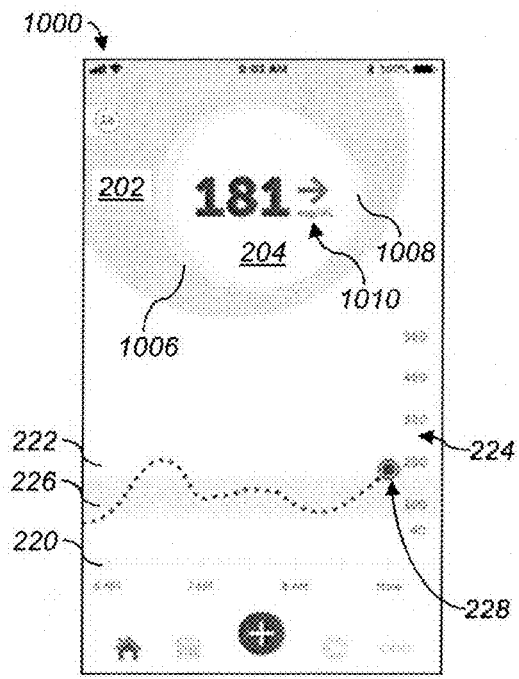
Figure 10B:
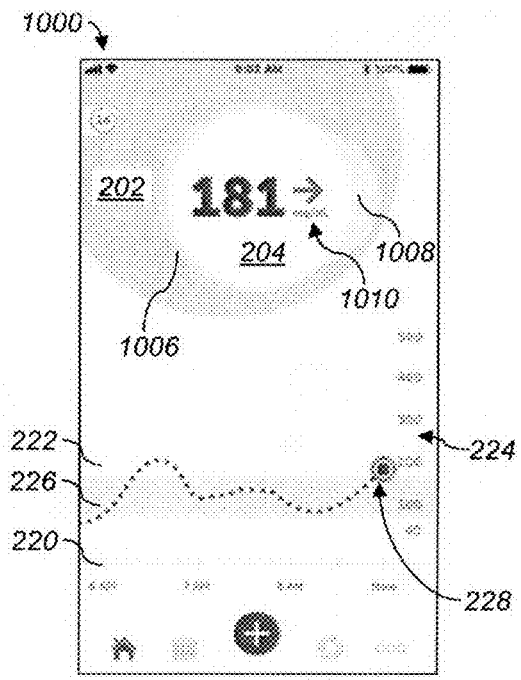

FIGS. 10A & 10B depict another graphical user interface 1000 in accordance with aspects of the invention. The animation includes periodically oscillating between the state of FIG. 10A and FIG. 10B. In this embodiment, the colored bubble 202 is red, indicating that the current analyte concentration level is above the target analyte (glucose) concentration level. As noted above, the determination that a concentration level is at, above, or below a target level or range is, in various embodiments, determined based on using a range of values, e.g., 10 units, around the target value. In addition, first and second trend indicating bubbles 1006, 1008, are configured to move to the right, as shown, and a right arrow indicator 1010 is further provided, in which each of the bubbles 1006, 1008 and indicator 1010 are configured to indicate a stable trend in the analyte concentration level.

Figure 11A:
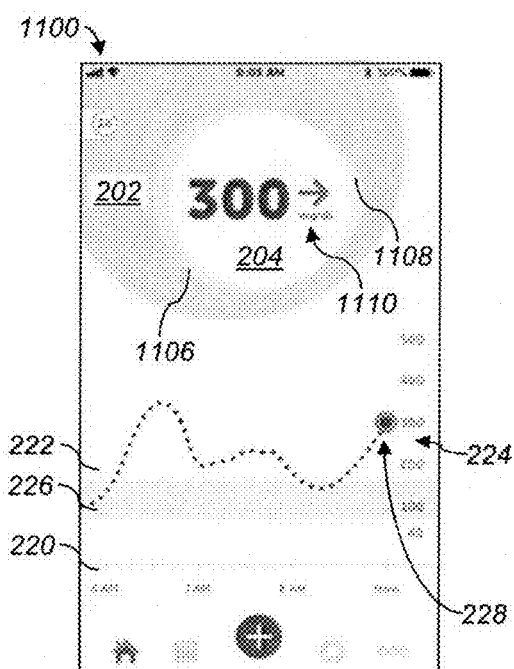
Figure 11B:
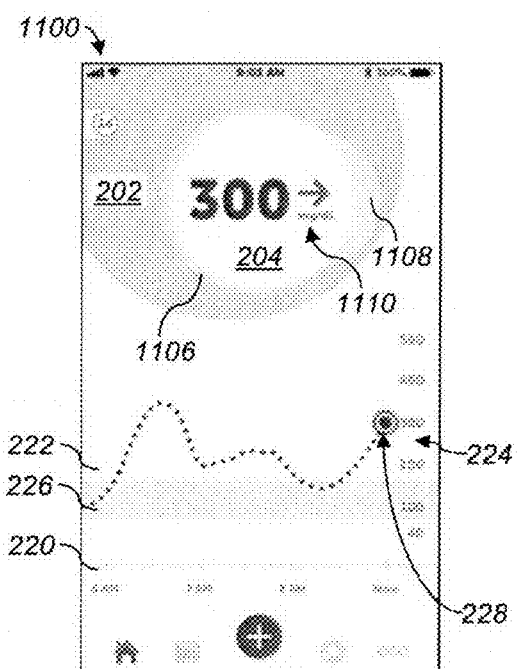

FIGS. 11A & 11B depict yet another graphical user interface 1100 in accordance with aspects of the invention. The animation includes periodically oscillating between the state of FIG. 11A and FIG. 11B. In this specific embodiment, the colored bubble 202 is red, indicating that the current analyte concentration level is above the target analyte concentration level stored by the processor of the system. In addition, first and second trend indicating bubbles 1106, 1108, are configured to move to the right of the animation, and a right arrow indicator 1110 is further provided, each of the latter bubbles 1106, 1108 and indicator 1110 being configured to indicate a stable trend in the analyte concentration level. In addition and according to this embodiment, the period of oscillation here may be faster than that of the animation of FIGS. 10A & 10B in order to indicate to the user a more severe excursion from desired concentration levels, and/or that the levels that are being displayed are not heading towards recovery (i.e., the host's target analyte concentration level).

Figure 12A:
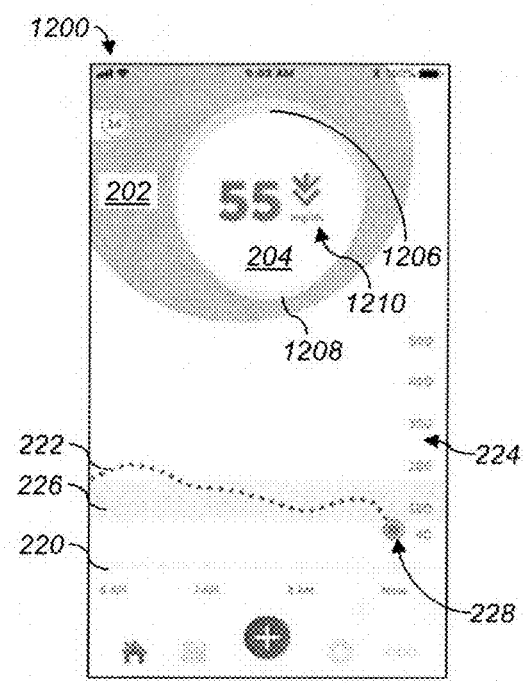
Figure 12B:
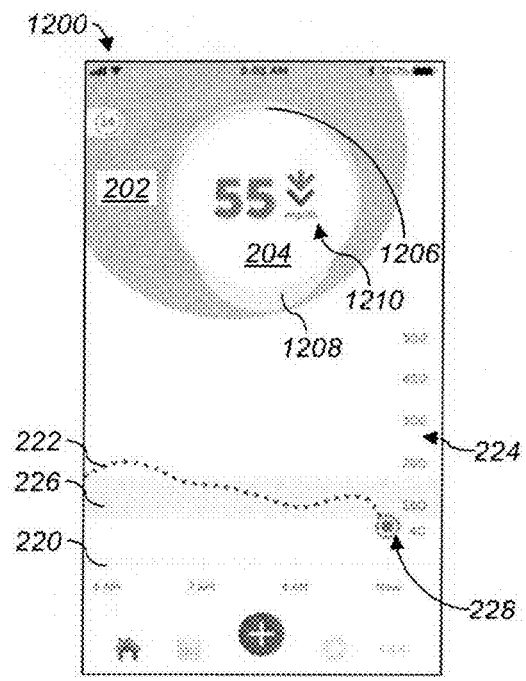

FIGS. 12A & 12B depict yet another graphical user interface 1200 in accordance with aspects of the invention. The animation includes periodically oscillating between the state of FIG. 12A and FIG. 12B. In this specific embodiment, the colored bubble 202 of the animation is blue, indicating that the current analyte concentration level is below the stored target analyte concentration level. In addition, first and second trend indicating bubbles 1206, 1208, move downward, and a double downward arrow indicator 1210 is provided, each of the foregoing to indicate a downward trend in the analyte concentration level.

Figure 13A:
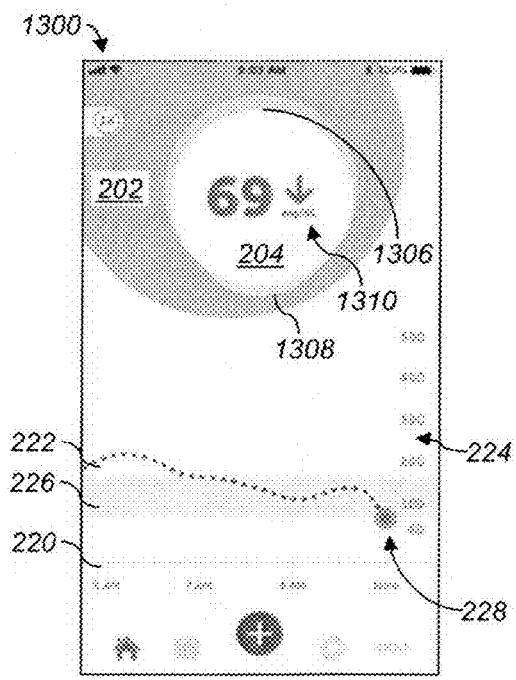
Figure 13B:
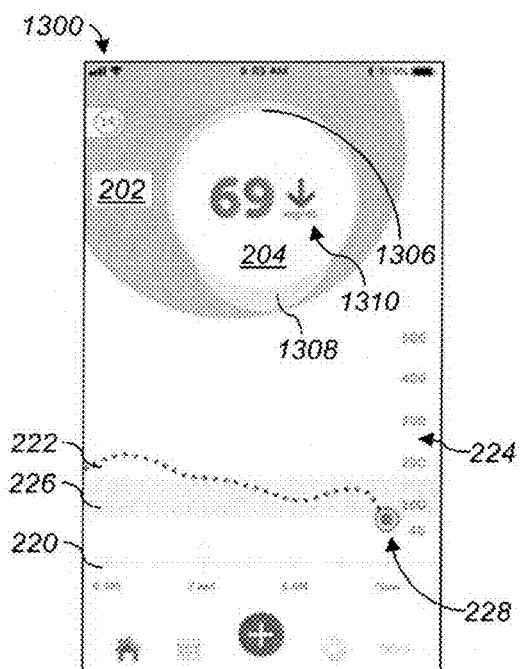

FIGS. 13A & 13B depict a graphical user interface 1300 in accordance with other aspects of the invention. The animation includes periodically oscillating between the state of FIG. 12A and FIG. 12B. In this specific embodiment, the colored bubble 202 is blue, indicating that the current analyte concentration level is below the target analyte concentration level or range. In addition, first and second trend indicating bubbles 1306, 1308, move downward, and a single downward arrow indicator 1310 is provided, each configured to indicate a downward trend in the analyte concentration level to a user. The period of oscillation in this version may be slower than that of the animation of FIGS. 12A & 12B, in order to indicate a less severe excursion from target analyte concentration levels.

Figure 14A:
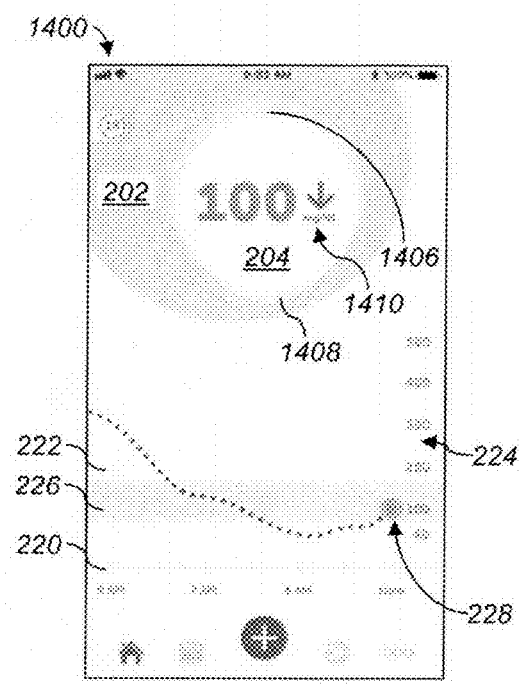
Figure 14B:
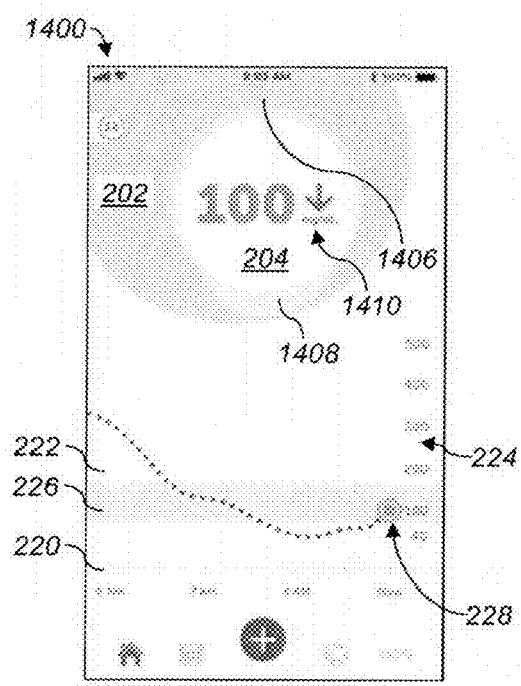

FIGS. 14A & 14B depict a graphical user interface 1400 in accordance with other aspects of the invention. The animation includes periodically oscillating between the state of FIG. 14A and FIG. 14B. In this specific embodiment, the colored bubble 202 is green, indicating that the current analyte concentration level is at or within the target analyte concentration range stored by the processor of the system. In addition, first and second trend indicating bubbles 1406, 1408, move downward, and a downward arrow indicator 1410 is provided, each of the latter being configured to indicate a downward trend in the analyte concentration level to the user.

Figure 15A:
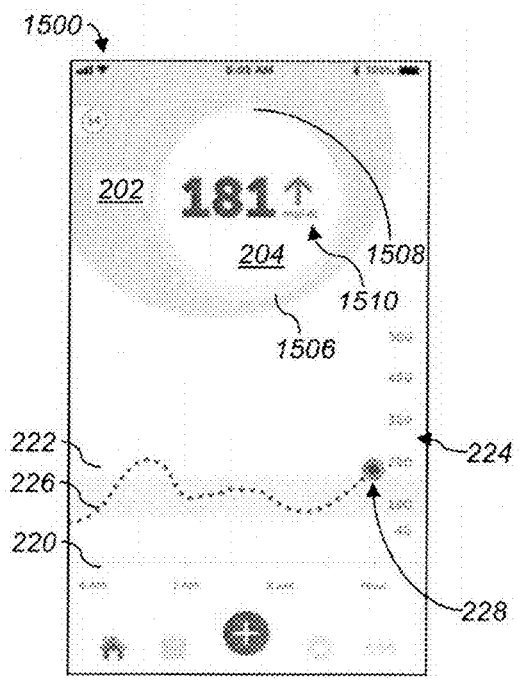
Figure 15B:
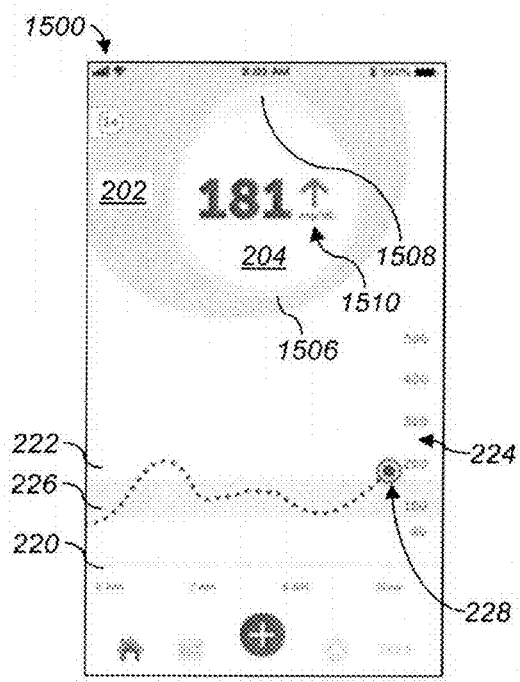

FIGS. 15A & 15B depict a graphical user interface 1500 in accordance with other various aspects. The animation includes periodically oscillating between the state of FIG. 15A and FIG. 15B. In this specific embodiment, the colored bubble 202 is red, indicating that the current analyte concentration level is above the target analyte concentration range, as stored by the processor of the system. In addition, first and second trend indicating bubbles 1506, 1508, move upward, and an upward arrow indicator 1510 is provided, each of the foregoing being configured to indicate an upward trend in the analyte concentration level of the host.

Figure 16A:
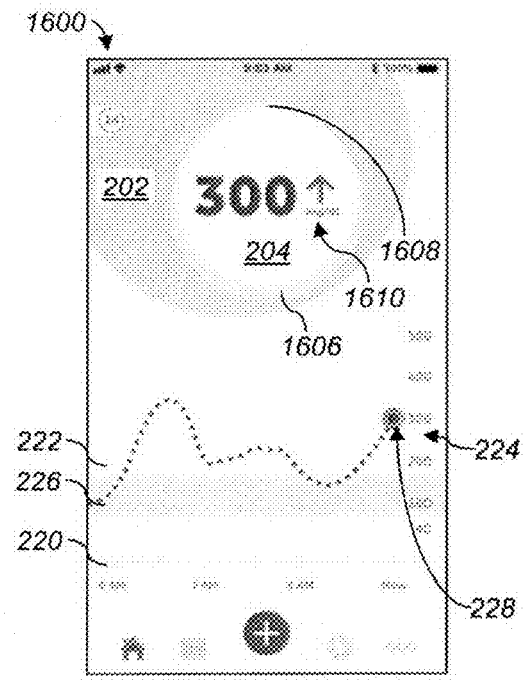
Figure 16B:
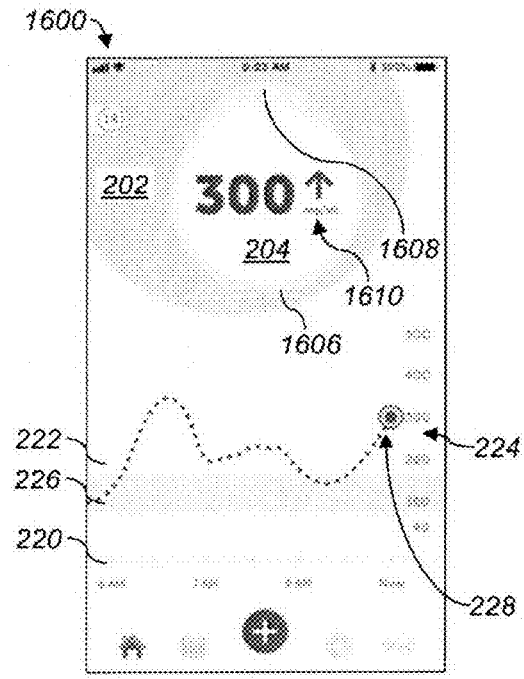

FIGS. 16A & 16B depict yet another example of a graphical user interface 1600 in accordance with aspect of the invention. The animation includes periodically oscillating between the state of FIG. 16A and FIG. 16B. In this specific embodiment, the colored bubble 202 is red, indicating that the current analyte concentration level is above the stored target analyte concentration range. In addition, first and second trend indicating bubbles 1606, 1608, move upward, and an upward arrow indicator 1610 is provided, each of the latter being configured to indicate an upward trend in the analyte concentration level of the host. The period of oscillation here may be faster than that of FIGS. 15A & 15B in order to indicate a more severe excursion from target analyte concentration levels.

Figure 17A:
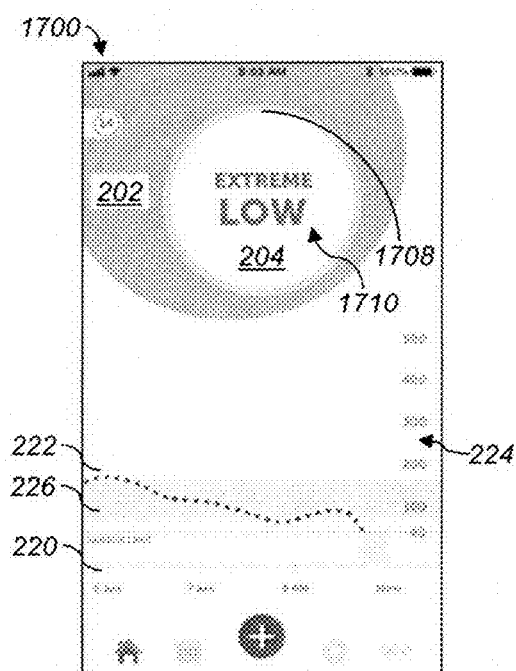
Figure 17B:
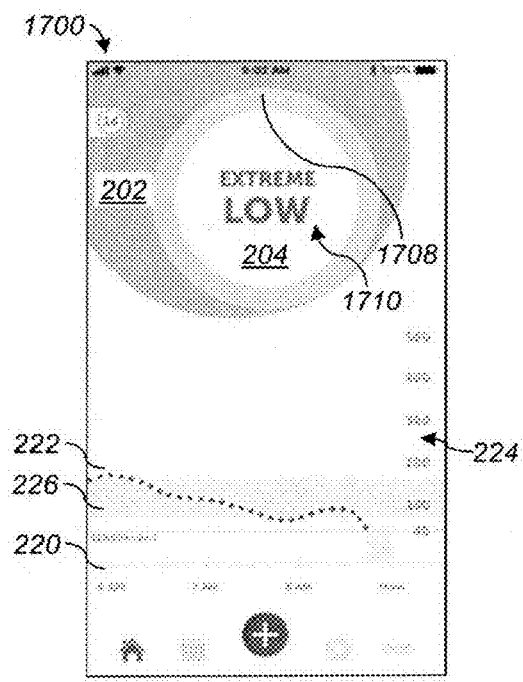

FIGS. 17A & 17B depict another graphical user interface 1700 in accordance with aspects of the invention. The animation includes periodically oscillating between the state of FIG. 17A and FIG. 17B. In this specific embodiment, the colored bubble 202 is blue, indicating that the current analyte concentration level is below that of the stored target analyte concentration range, and as shown, the value presented in the white bubble 204 indicates that the detected analyte concentration level is an extreme low. In addition, the second trend indicating bubble 1708 according to this version is configured to pulsate at a predetermined interval between the positions shown in FIGS. 17A & 17B in order to indicate this extreme low condition. In such a case, a trend arrow indicator is unable to be displayed, because the direction of the bubbles 1706, 1708 follow the trend when an arrow indicator is present. Furthermore, the timeline 220 in the lower portion of this animation indicates that the sensor limit, i.e., the limit of the sensor's reportable range, has been reached.

Figure 18A:
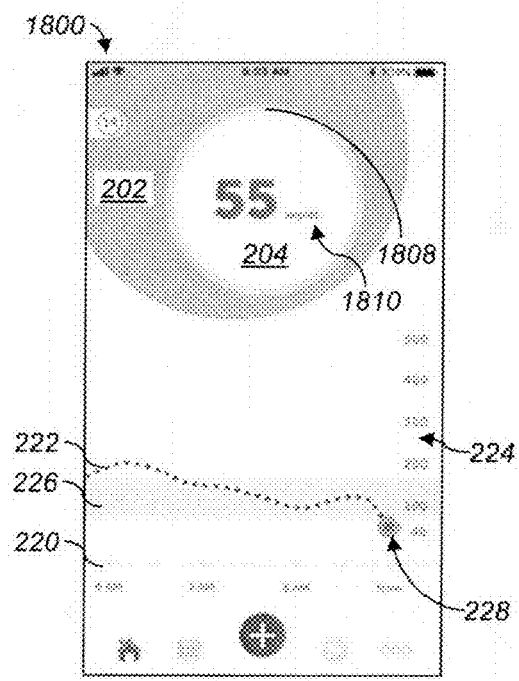
Figure 18B:
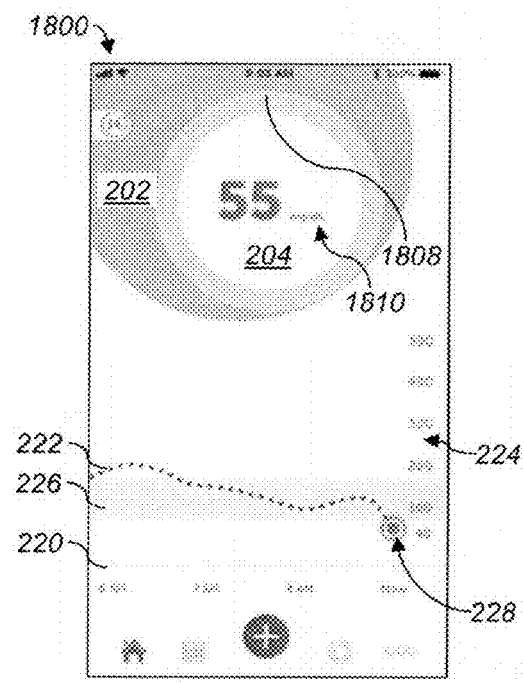

FIGS. 18A & 18B depict yet another graphical user interface 1800 in accordance with aspects of the invention. The animation includes periodically oscillating between the state of FIG. 18A and FIG. 18B. In this specific embodiment, the colored bubble 202 is blue, indicating that the current analyte concentration level is below the stored target analyte concentration range. In addition, one of the trend indicating bubbles 1808 pulsates between the positions shown in FIGS. 18A & 18B in order to indicate that a trend cannot be represented in the animation and hence no arrow indicator is presented to the user.

Figure 19A:
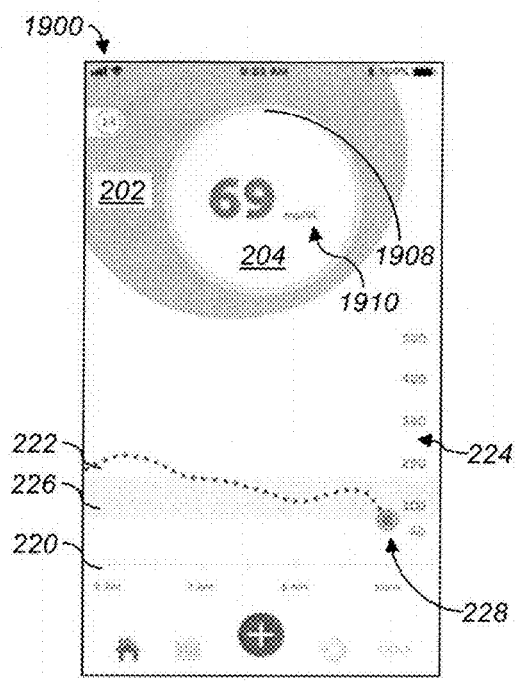
Figure 19B:
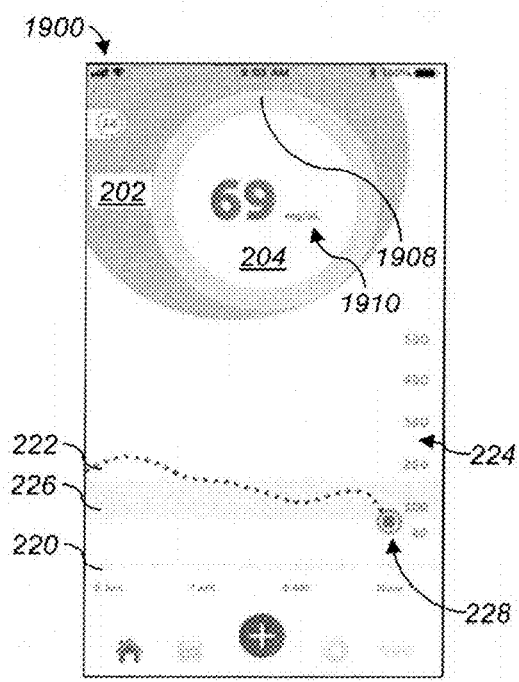

FIGS. 19A & 19B depict a graphical user interface 1900 in accordance with aspects of the invention. The animation includes periodically oscillating between the state of FIG. 19A and FIG. 19B. In this embodiment, the colored bubble 202 is blue, indicating that the current analyte concentration level is below the stored target analyte concentration range. In addition, one of the trend indicating bubbles 1908 is configured to pulsate between the positions shown in FIGS. 19A & 19B in order to indicate that a trend cannot be represented to a user.

Figure 20A:
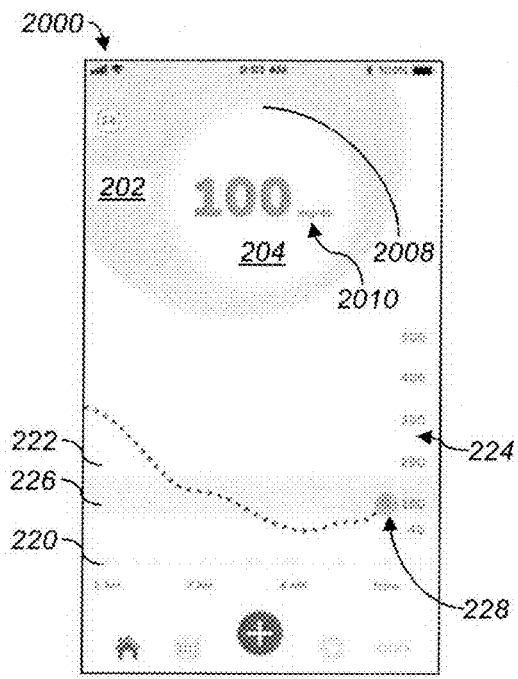
Figure 20B:
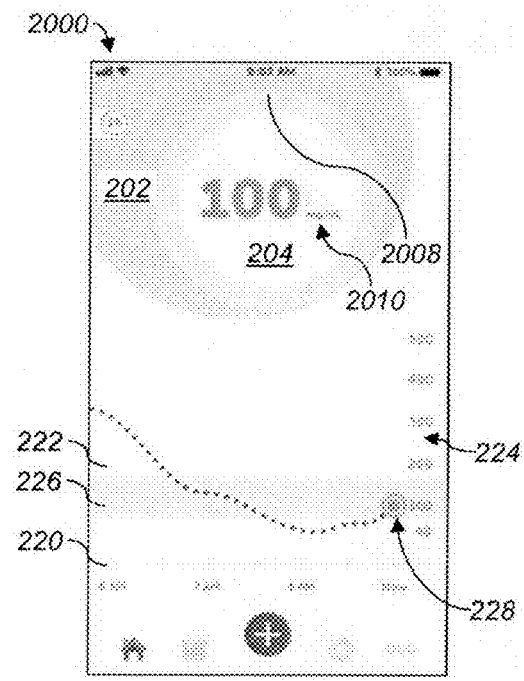

FIGS. 20A & 20B depict a graphical user interface 2000 in accordance with other aspects of the invention. The animation includes periodically oscillating between the state of FIG. 20A and FIG. 20B. In this embodiment, the colored bubble 202 is green, indicating that the current analyte concentration level is within the stored target analyte concentration range. In addition, one of the trend indicating bubbles 2008 is configured according to this version to pulsate between the positions shown in FIGS. 20A & 20B to indicate that a trend cannot be reported to a user.

Figure 21A:
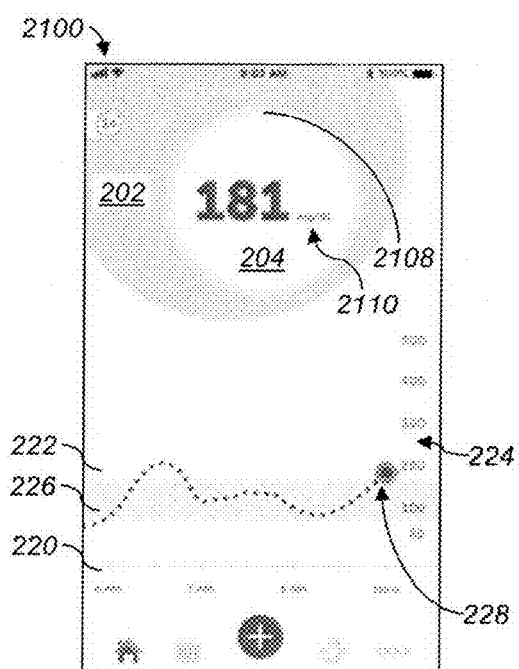
Figure 21B:
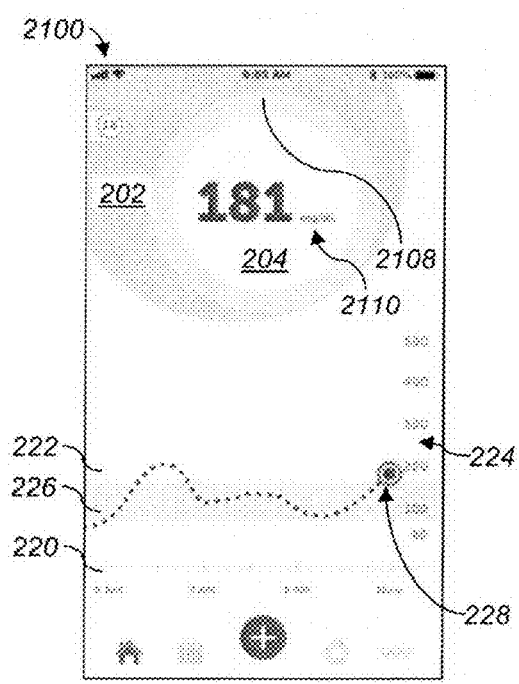

FIGS. 21A & 21B depict a graphical user interface 2100 in accordance with other aspects of the invention. The animation includes periodically oscillating between the state of FIG. 21A and FIG. 21B. In this specific embodiment, the colored bubble 202 is red, indicating that the current analyte concentration level is above the stored target analyte concentration range. In addition, one of the trend indicating bubbles 2108 is configured to pulsate between the positions shown in FIGS. 21A & 21B to indicate that a trend cannot be reported.

Figure 22A:
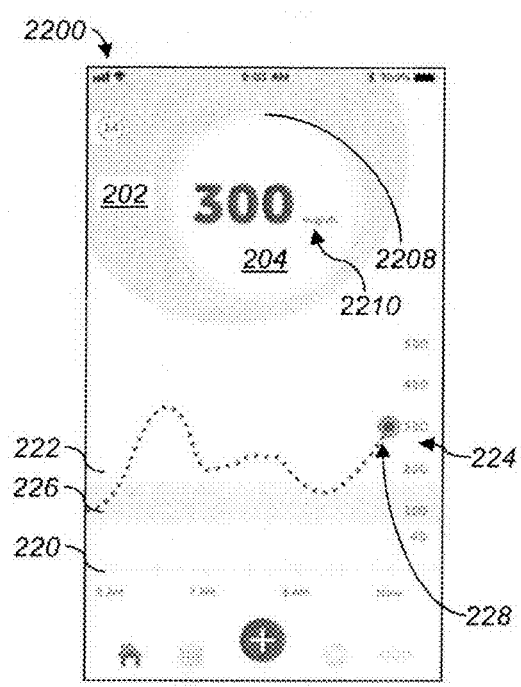
Figure 22B:
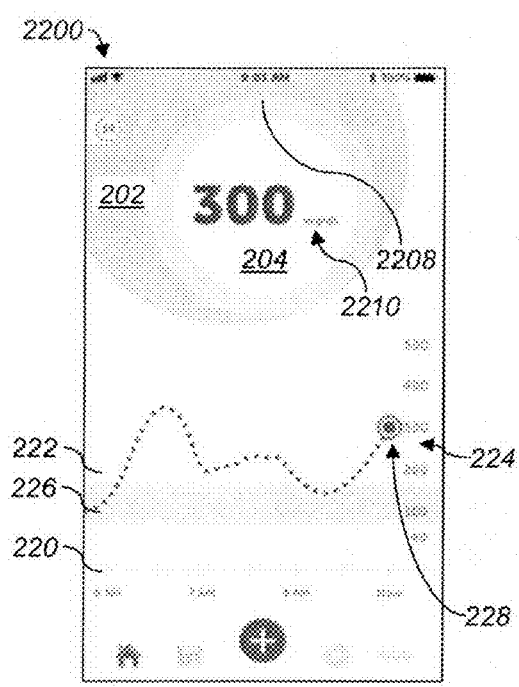

FIGS. 22A & 22B depict another graphical user interface 2200 in accordance with aspects of the invention. The animation includes periodically oscillating between the state of FIG. 22A and FIG. 22B. In this specific embodiment, the colored bubble 202 is red, indicating that the current analyte concentration level is above the stored target analyte concentration range. In addition, at least one of the trend indicating bubbles 2208 is configured to pulsate between the positions shown in FIGS. 22A & 22B to indicate that a trend cannot be reported. The period of pulsation here may be faster than that of FIGS. 21A & 21B to indicate a more severe excursion from target analyte concentration levels.

Figure 23A:
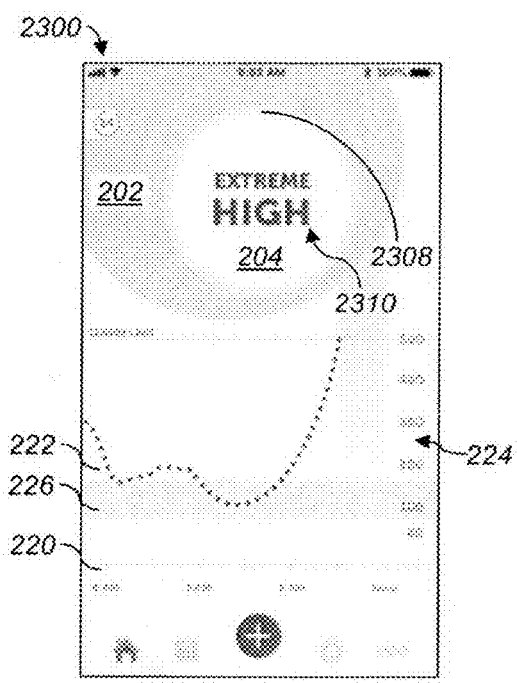
Figure 23B:
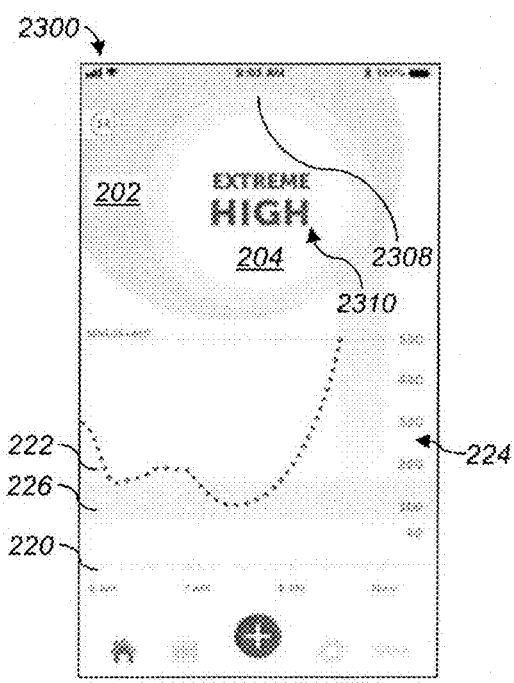

FIGS. 23A & 23B depict another graphical user interface 2300 in accordance with aspects of the invention. The animation includes periodically oscillating between the state of FIG. 23A and FIG. 23B. In this embodiment, the colored bubble 202 of the animation is red, indicating that the current analyte concentration level is above the stored target analyte concentration range, and according to this embodiment, the value presented in the white bubble 204 indicates that the detected level is an extreme high. In addition, at least one of the trend indicating bubbles 2308 is configured to pulsate between the positions shown in FIGS. 23A & 23B to indicate this extreme high condition. Furthermore and according to this embodiment, the red gradient depicted in the body of and above the graph indicates that the limit of the sensor's reportable range has been reached.

FIG. 24 depicts an embodiment of an animation decision matrix for determining which animated graphical user interface to present on the display unit of FIG. 1. As shown in FIG. 24, the current trend and current analyte concentration level, which may be determined by the processor, are used to determine the periodicity or speed of the animation. The rows (as shown on the Y axis) show the current trend as rapidly rising, rising, steady, falling, rapidly falling, or pulsing, which may be used to choose one of the graphical user interfaces of FIGS. 2A-23B. The columns (on the X axis) show the current analyte concentration level as being extreme high (501+ mg/dL), very high (500-300 mg/dL), high (299-X mg/dL; where X is the user's target high), in range (X-Y mg/dL; where Y is the user's target low), low (Y-56 mg/dL), very low (55-40 mg/dL), extreme low (39-0 mg/dL), or urgent low. Where the rows and column intersect in the table, the level indicates which speed to choose. For example: L3 corresponds to super-fast and blinking arrows with a duration of 0.4 seconds; L2 corresponds to super-fast with a duration of 0.4 seconds; L1 corresponds to fast with a duration of 1 second; and L0 corresponds to slow with a duration of 2 seconds. In other examples, different durations may be used.

By way of summary, FIGS. 25A-25I depict embodiments of animated graphical user interface elements, in accordance with one or more aspects set forth herein.

Figure 25A:
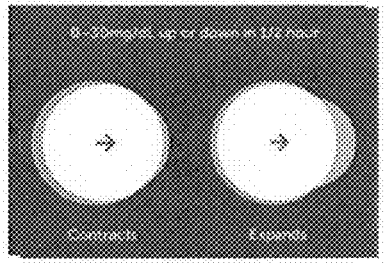
FIGS. 25A-25I depict various embodiments of animated graphical user interface elements, in accordance with one or more aspects set forth herein.

FIG. 25A shows that an increase of 0-30 mg/dL in a half-hour would trigger a rightward animation.

Figure 25B:
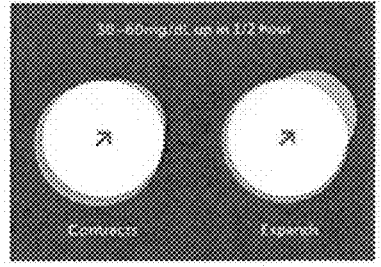

FIG. 25B shows that an increase of 30-60 mg/dL in a half-hour would trigger an animation that is up and to the right.

Figure 25C:
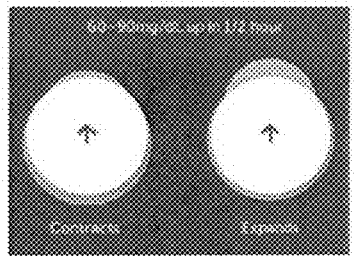

FIG. 25C shows that an increase of 60-90 mg/dL in a half-hour would trigger an upward animation.

Figure 25D:
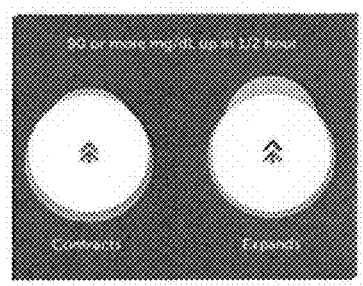

FIG. 25D shows that an increase of 90+ mg/dL in a half-hour would trigger an upward animation with two arrows.

Figure 25E:
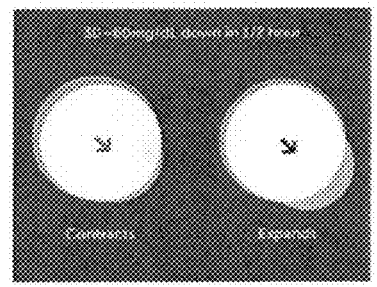

FIG. 25E shows that a decrease of 30-60 mg/dL in a half-hour would trigger a downward and to the right animation.

Figure 25F:
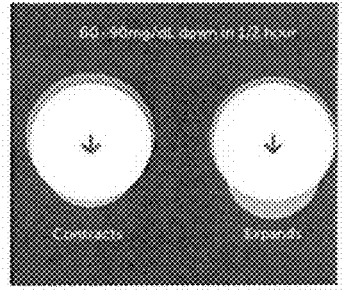

FIG. 25F shows that a decrease of 60-90 mg/dL in a half-hour would trigger a downward animation.

Figure 25G:
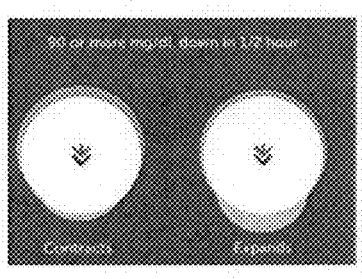

FIG. 25G shows that a decrease of 90+ mg/dL in a half-hour would trigger a downward animation with two arrows.

Figure 25H:
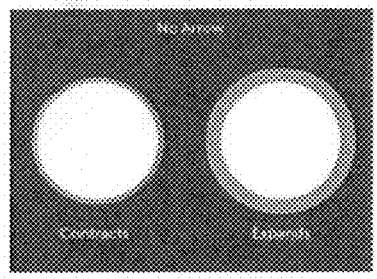

FIG. 25H shows a pulsing animation without an arrow as noted above.

Figure 25I:
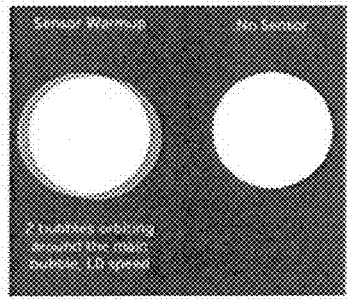

FIG. 25I shows an animation with 2 bubbles orbiting, e.g., for use during sensor warmup, along with no bubble shown when there is no sensor.

Figure 26:
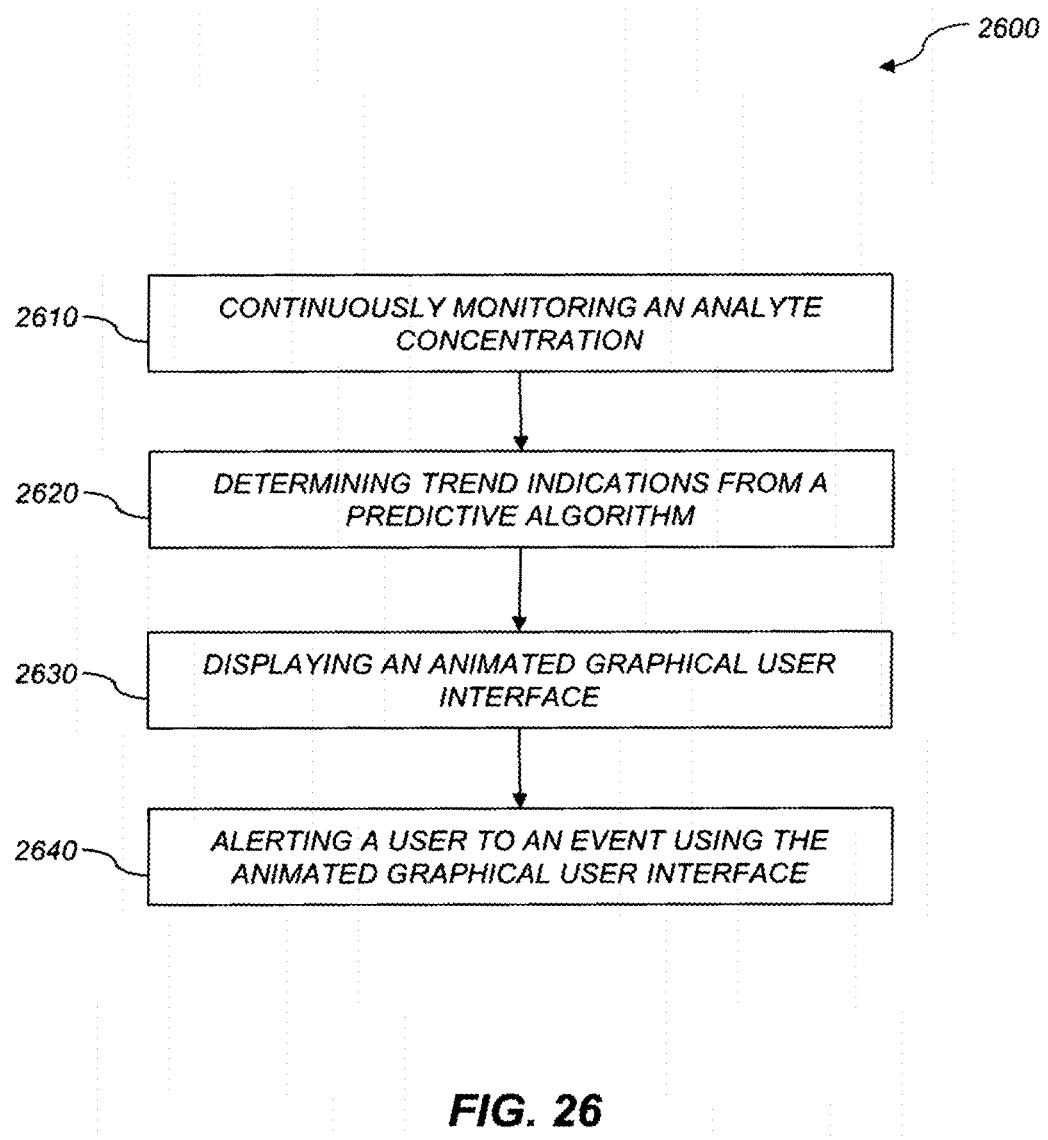
FIG. 26 is a flowchart depicting a method of alerting a user using an animated graphical user interface, in accordance with one or more aspects set forth herein.

FIG. 26 is a flowchart depicting a method 2600 of alerting a user using an animated graphical user interface, such as those previously described. The method 2600 at block 2610 continuously monitors an analyte concentration block of a physiological fluid. The method 2600 at block 2620 determines trend indications form a predictive algorithm, which can be stored in a processor. The method 2600 at block 2630 displays, using a graphical user interface, historical analyte concentration levels and a trend indication animation. The trend indication animation comprises a visual element configured by the at least one processor to have a periodic motion between a first position and a second position on the display in one of a plurality of trend directions. The trend direction of the periodic motion between the first and second positions indicates whether the analyte concentration is trending above a target analyte concentration level, or at a target analyte concentration level. The visual element is further configured with a period of the periodic element is further configured with a period of the periodic motion between the first and second positions in order to indicate a severity of an excursion of the analyte concentration as compared with the target analyte concentration level. The method at block 2640 alerts a user via the graphical user interface animations noted above.

Figure 27:
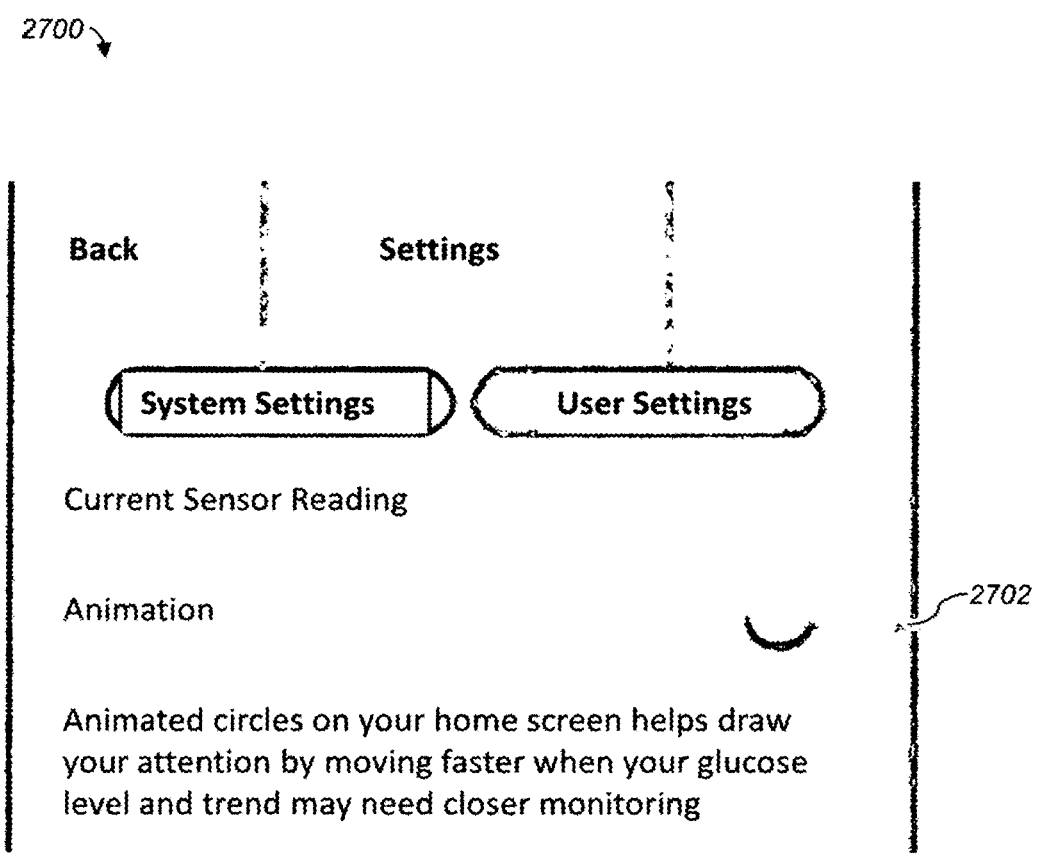
FIG. 27 depicts an embodiment of a graphical user interface element for enabling user settings, e.g., for use with the graphical user interfaces of FIGS. 2A-23B, in accordance with one or more aspects set forth herein.

FIG. 27 depicts an embodiment of a graphical user interface 2700 which allows the inclusion of one or more user settings. The graphical user interface element 2700 may be used with the graphical user interfaces of FIGS. 2A-23B. For example, the animations described above may be turned off by default in the programming of the processor of the system. In such a case, graphical user interface element 2702 may be used to turn on (or off) animations.

Figure 28:
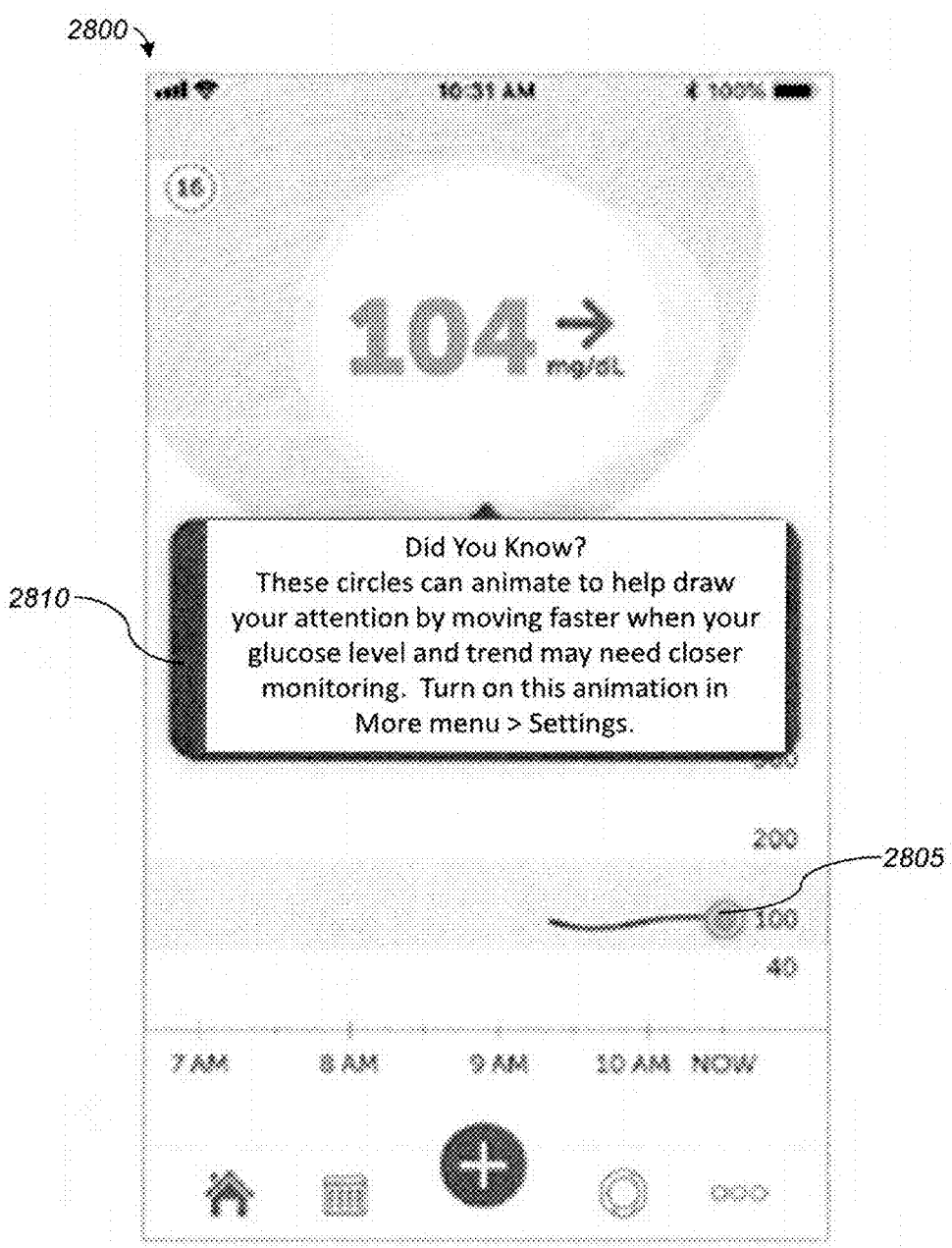
FIG. 28 depicts an embodiment directed to a tip or similar prompt for enabling animations, e.g., for use with the graphical user interfaces of FIGS. 2A-23B, in accordance with one or more aspects set forth herein.

FIG. 28 depicts an embodiment of a graphical user interface 2800 that includes a graphical user interface element 2810. In one embodiment, graphical user interface element 2810 provides a tip or other form of prompt for enabling animations, e.g., for use with the graphical user interfaces of FIGS. 2A-23B. For example, the graphical user interface element 2810 may be displayed to a user if the user has not tried using animation within three days (or any other configurable period) of the user beginning to use the system. In addition, the graphical user interface element 2810 can present a demonstration or trial mode. These elements can be selected to show only during certain hours of the day.

According to at least one specific implementation and if the animation is turned on, the current analyte reading animation (or "now dot") 2805 will begin to be animated to pulse at a rate of speed that is commensurate to the severity of the reading, as previously disclosed above with respect to the event indicating bubbles of the animation. In another example, the animation may include a series of readings and/or trend arrow(s). In such a case, the animation may be different depending on a combination of the reading value and the arrow.

Figure 29:
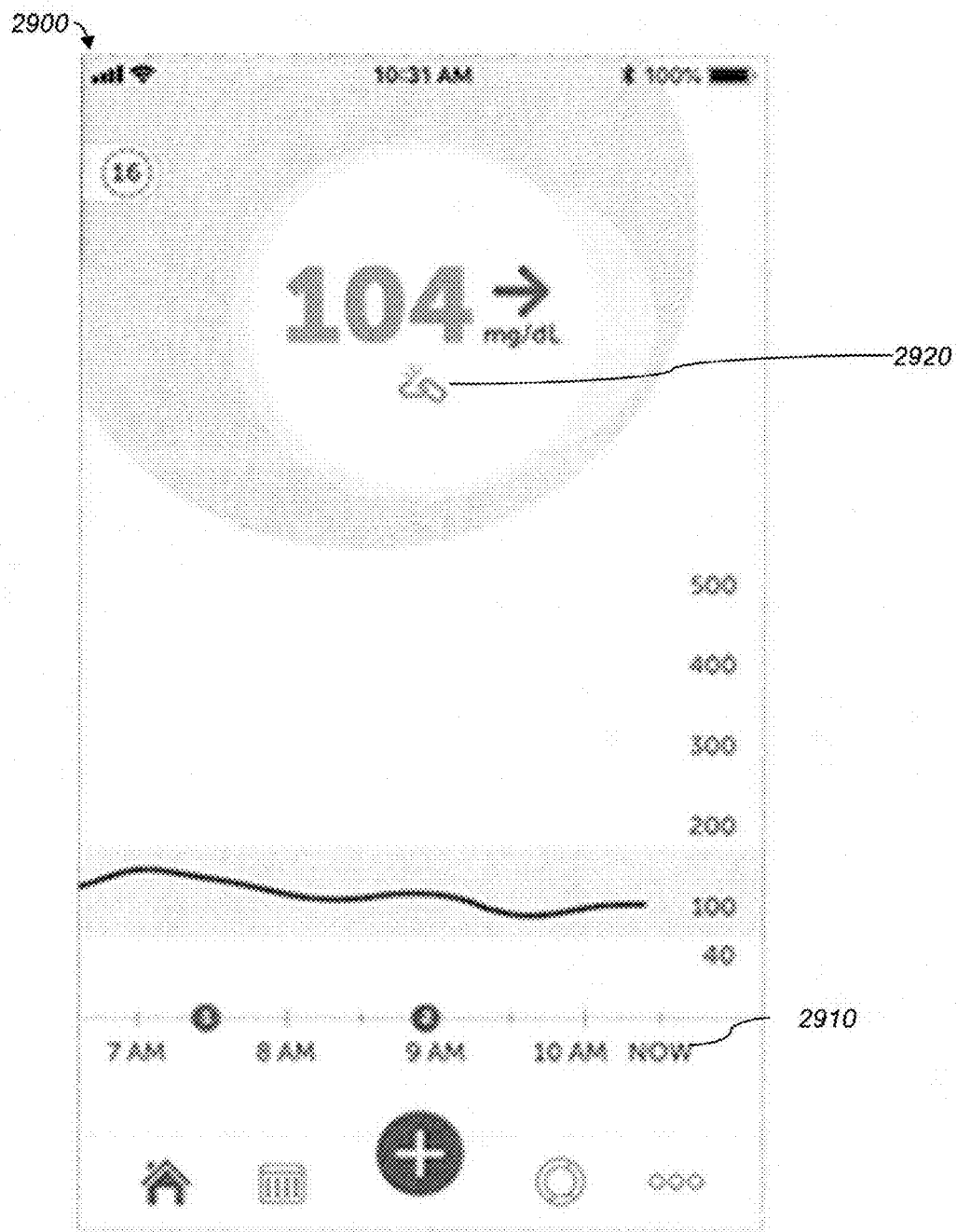
FIG. 29 depicts an embodiment in which a current analyte reading animation disappears to indicate a lack of connectivity of the sensor, e.g., for use with the graphical user interfaces of FIGS. 2A-23B, in accordance with one or more aspects set forth herein.

FIG. 29 depicts an embodiment of a graphical user interface 2900 in which a current analyte reading animation element 2910 disappears in order to indicate lack of connectivity to the user. Once connectivity is restored, the animation element 2910 will again be displayed. In addition, an icon 2920 indicative of a loss of connectivity may also be presented to a user, e.g., to indicate that connection has been lost, or to indicate that the sensor is reporting that the data is not reliable. For instance, the icon 2920 may indicate lack of connectivity or staleness of data. In one embodiment, the icon 2929 may be a broken link icon. In another embodiment, a different broken link icon may be presented under the current reading when the reading is stale (e.g., older than one minute, or some other configurable number of minutes, due to Signal Loss or Unstable Reading/No Reading condition and this icon can then stay up for up to five minutes, or some other configurable number of minutes. In another embodiment, after a specified time period without any new readings, a stale reading icon may be replaced or augmented with a Signal Loss or No Reading message on displayed on the screen. In another embodiment, once a new reading is available, the now dot indicator may return (with pulsing) and the Broken Link Icon goes away.

Figure 30A:
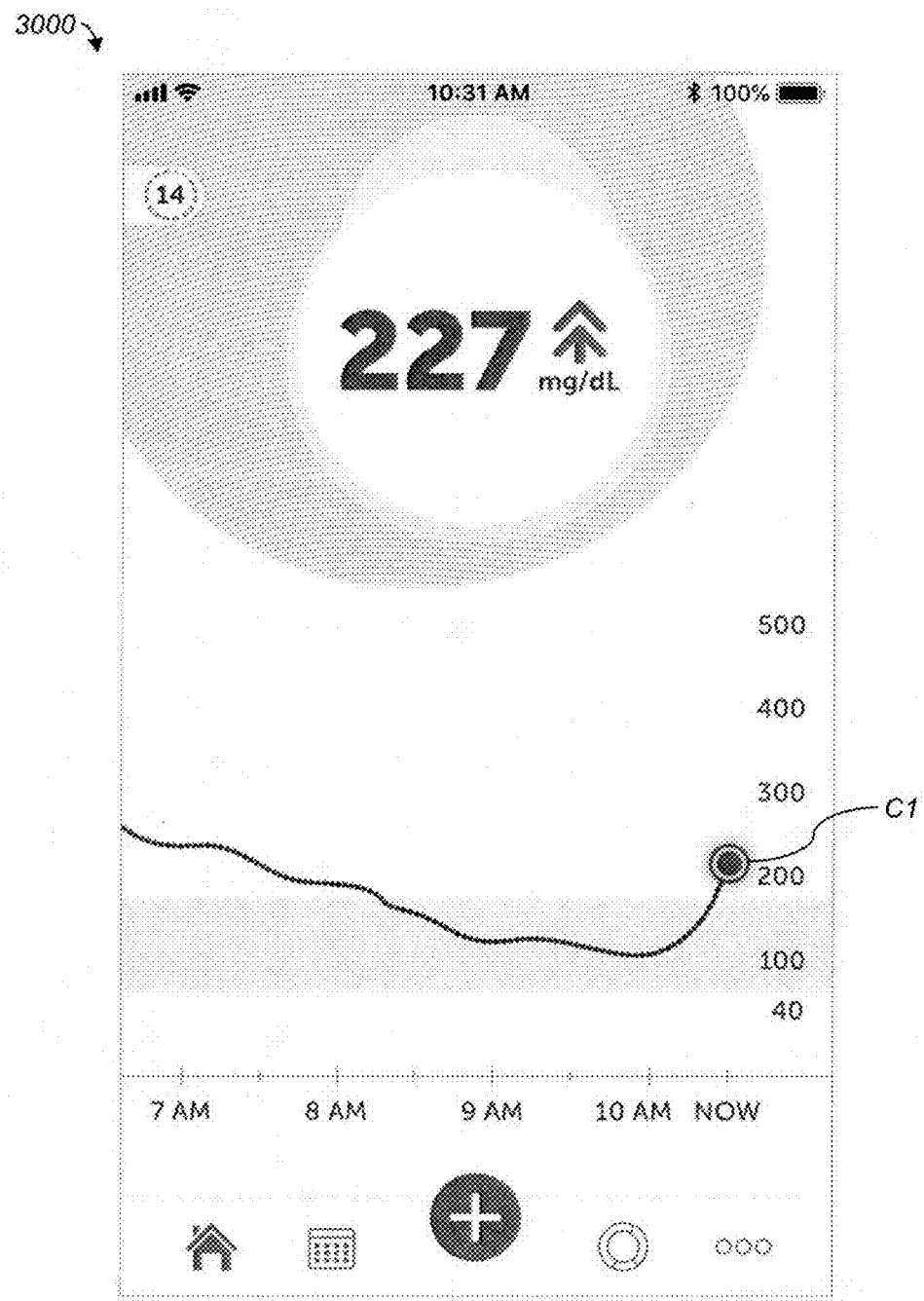
FIGS. 30A-30C depicts an embodiment in which a current analyte reading animation changes colors in order to indicate target range thresholds, e.g., for use with the graphical user interfaces of FIGS. 2A-23B, in accordance with one or more aspects set forth herein.
Figure 30B:
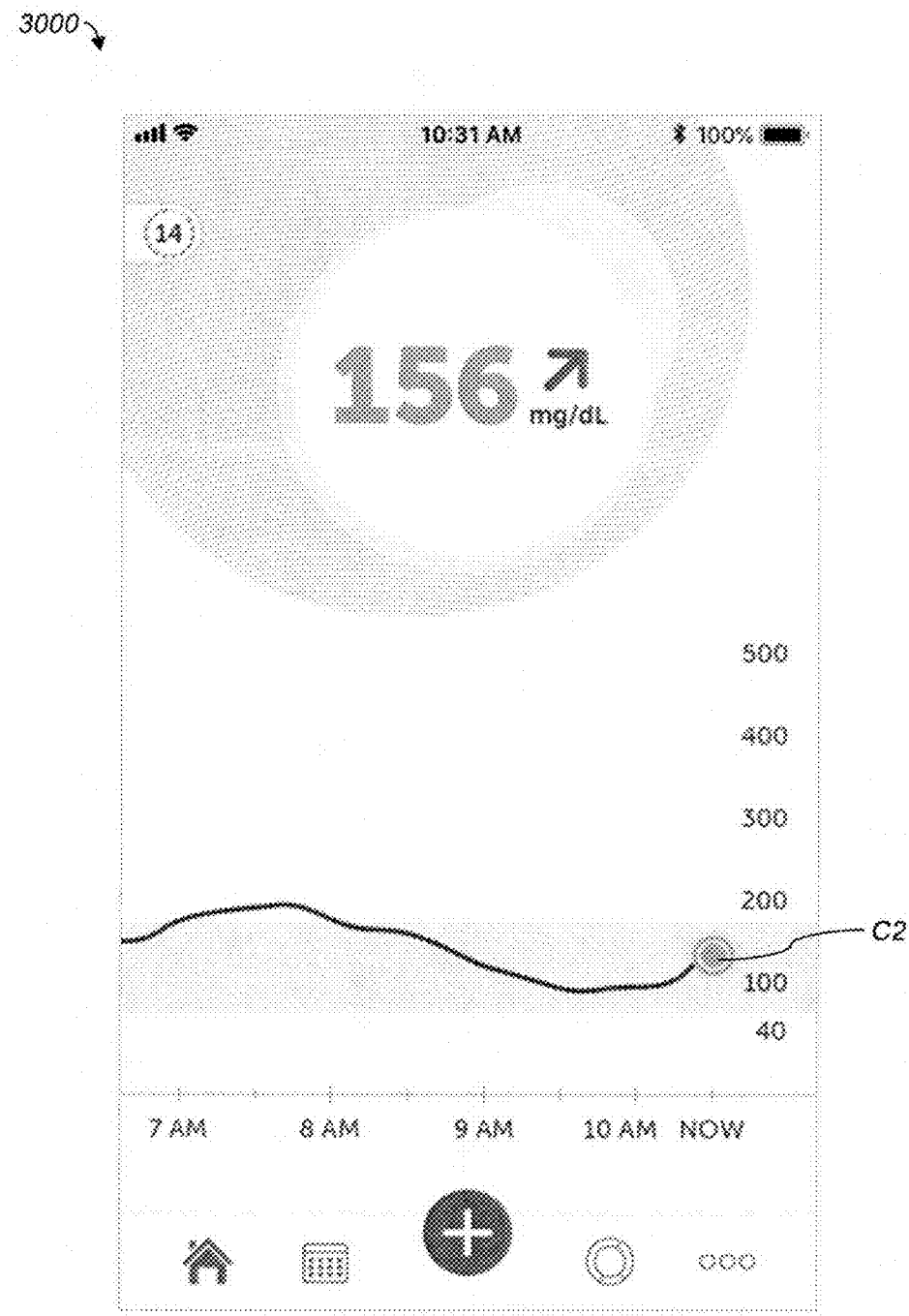
Figure 30C:
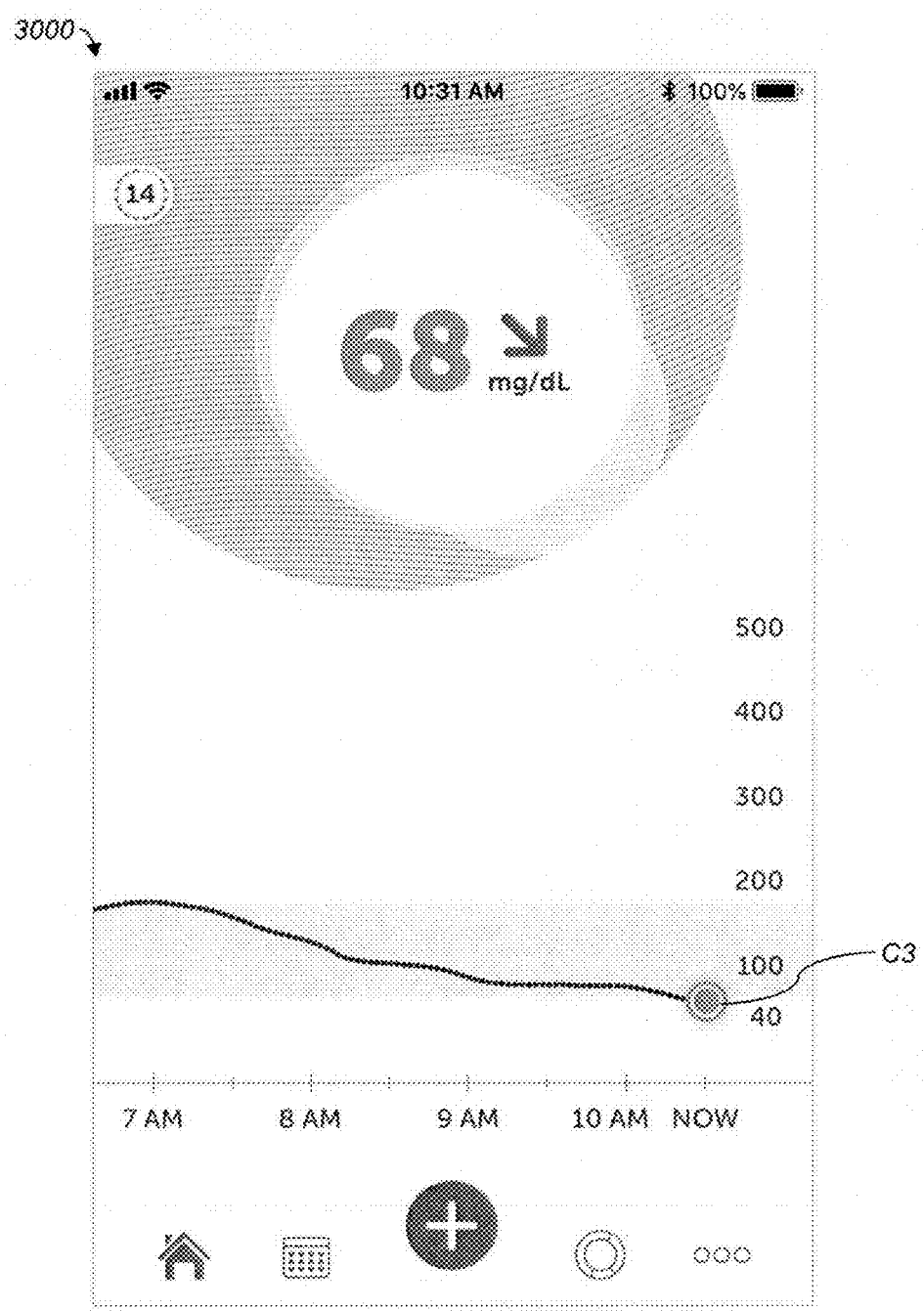

FIGS. 30A-30C depicts an embodiment of a graphical user interface 3000 in which a current analyte reading animation element changes colors to indicate the current reading relative to target range threshold. For example, FIG. 30A shows using a first color C1 such as red to indicate that the reading is above target. FIG. 30B shows using a second color C2 such as green to indicate that the reading is at target. FIG. 30C shows using a third color C3 such as blue to indicate that the reading is below target.

Embodiments of the present disclosure may include a system, a method, and/or a computer program product. The computer program product may include a computer readable storage medium (or media) having computer readable program instructions thereon for causing a processor to carry out aspects of set forth herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the certain embodiments may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects set forth herein.

Embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A system for continuously monitoring analyte concentration levels in a physiological fluid, the system comprising:
   a sensor;
   a transmitter;
   one or more processors; and
   a unit for receiving data from the sensor comprising a display for outputting a graphical user interface, the display being controlled by the one or more processors to display, using the graphical user interface, historical analyte concentration levels and a trend indication animation, the trend indication animation comprising a first visual element configured by the one or more processors to have a periodic motion between a first position and a second position on the display in one of a plurality of trend directions, wherein the trend direction of the periodic motion between the first and second positions indicates whether the analyte concentration is increasing or decreasing and the rate of change of the analyte concentration level, and in which the first visual element is further configured with a period of the periodic motion between the first and second positions in order to indicate a severity of an excursion of the analyte concentration levels, wherein the first visual element comprises two trend-indicating bubbles disposed beneath a static center bubble on the graphical user interface wherein the two trend-indicating bubbles are configured by the one or more processors to move in unison relative to the static center bubble in said one of the plurality of trend directions between the first position and the second position in accordance with the periodic motion and in which a portion of one of the trend-indicating bubbles is caused to emerge from beneath the static center bubble in the second position and a portion of the other of the trend-indicating bubbles is caused to move further beneath the static center bubble, wherein the combined periodic movement of the pair of trend-indicating bubbles between the first and second position relative to the static center bubble provides a clear indication of a trend in one of the plurality of trend directions.

2. The system of claim 1, wherein the trend indication animation further comprises at least a second visual element configured by the one or more processors and comprising one or more indicators to visualize the trend direction on the graphical user interface.

3. The system of claim 1, wherein the periodic motion is an oscillation between the first position and the second position, in which a period of the oscillation is adjustable by the one or more processors.

4. The system of claim 1, wherein the trend indication animation is disabled during a specified time period.

5. The system of claim 1, wherein the one or more processors determines the trend of the analyte concentration based on historical measurements.

6. The system of claim 1, wherein the static center bubble of the first visual element includes a current analyte concentration-reading.

7. The system of claim 2, wherein at least a portion of the first visual element or the second visual element comprises more than one color.

8. The system of claim 1, wherein the analyte concentration level comprises a glucose concentration level.

9. A method for alerting a user of an event related to an analyte concentration in a physiological fluid, the method comprising:
continuously monitoring the analyte concentration of the physiological fluid;
determining a trend of the analyte concentration based on historical measurements;
displaying, using a graphical user interface, historical analyte concentration levels and a trend indication animation; and
causing the trend indication animation comprising a first visual element configured by at least one processor to have a periodic motion between a first position and a second position on the display in one of a plurality of trend directions, wherein the trend direction of the periodic motion between the first and second positions indicates whether the analyte concentration is increasing or decreasing and the rate of change of the analyte concentration level, further providing the first visual element with a changeable period of the periodic motion between the first and second positions to indicate a severity of an excursion of the analyte concentration and wherein the first visual element comprises two trend-indicating bubbles disposed beneath a static center bubble in the graphical user interface, wherein the two trend-indicating movable bubbles are configured to move in unison in the trend direction between the first and second positions relative to the static center bubble and according to the periodic motion and in which a portion of one of the two trend-indicating bubbles is caused to emerge from beneath the static bubble in the second position and a portion of the other of the two trend-indicating bubbles is caused to move further beneath the static center bubble, wherein the combined periodic movement of the two trend-indicating bubbles between the first and second position relative to the static center bubble provides a clear indication of a trend in one of the plurality of trend directions.

10. The method of claim 9, further comprising displaying, using the graphical user interface, a current analyte value animation that pulses with a period of the periodic motion and changes color based on the severity of the excursion of the analyte concentration.

11. The method of claim 9, further comprising:
displaying at least a second visual element comprising one or more arrows indicating the trend direction on the graphical user interface, wherein the one or more arrows are blinking.

12. A graphical user interface for alerting a user of events based on continuous monitoring of an analyte concentration in a physiological fluid, the graphical user interface being displayed on a display and comprising:
historical analyte concentration levels; and
a trend indication animation, the trend indication animation comprising a first visual element configured by at least one processor to have a periodic motion between a first position and a second position on the display in one of a plurality of trend directions, wherein the trend direction of the periodic motion between the first and second positions indicates whether the analyte concentration is increasing or decreasing and the rate of change of the analyte concentration level, and in which the first visual element is further configured with a period of the periodic motion between the first and second positions in order to indicate a severity of an excursion of the analyte concentration, wherein the first visual element comprises a pair of trend-indicating bubbles disposed beneath a static center bubble in the graphical user interface and in which the pair of trend-indicating bubbles move in unison between the first and second positions relative to the static center bubble and in accordance with the periodic motion in one of the plurality of trend directions and in which a portion of one of the trend-indicating bubbles is caused to emerge from beneath the static bubble in the second position and a portion of the other of the trend-indicating bubbles is caused to move further beneath the static center bubble, wherein the combined periodic movement of the pair of trend-indicating bubbles between the first and second position relative to the static center bubble provides a clear indication of a trend in one of the plurality of trend directions.

13. The graphical user interface of claim 12, wherein the trend indication animation comprises at least a second visual element configured by the one or more processors and comprising one or more directional indicators indicating the trend direction on the graphical user interface.

14. The graphical user interface of claim 12, wherein the periodic motion is an oscillation between the first position and the second position, and the period of the oscillation is adjustable by the at least one processor.

15. The graphical user interface of claim 12, wherein the trend indication animation indicates the severity of an excursion.

16. The graphical user interface of claim 12, wherein the static center bubble of the first visual element includes a current analyte concentration reading.

17. The graphical user interface of claim 13, wherein at least a portion of the first visual element and the second visual element comprises more than one color.

18. The graphical user interface of claim 16, in which at least a portion of the first visual element and the second visual element is displayed in blue if the current analyte concentration reading is below a predetermined threshold, displayed in green if the current analyte concentration reading is within the predetermined threshold, and displayed in red if the current analyte concentration reading is above the predetermined threshold.

* * * * *